US012806275B2

(12) United States Patent
Huh et al.

(10) Patent No.: US 12,806,275 B2
(45) Date of Patent: Nov. 24, 2026

(54) INTRATYMPANIC DRUG CONTROLLED RELEASE-TYPE FORMULATION COMPRISING N-ACYLATED GLYCOL CHITOSAN

(71) Applicant: The Industry & Academic Cooperation in Chungnam National University (IAC), Daejeon (KR)

(72) Inventors: Kang Moo Huh, Daejeon (KR); Da Hae Kim, Daejeon (KR); Yong-Ho Park, Daejeon (KR); Ji Hyun Park, Daejeon (KR)

(73) Assignee: The Industry & Academic Cooperation in Chungnam National University (IAC), Daejeon (KR)

( * ) Notice: Subject to any disclaimer, the term of this patent is extended or adjusted under 35 U.S.C. 154(b) by 331 days.

(21) Appl. No.: 18/693,644

(22) PCT Filed: Sep. 19, 2022

(86) PCT No.: PCT/KR2022/013938
§ 371 (c)(1),
(2) Date: Mar. 20, 2024

(87) PCT Pub. No.: WO2023/054951
PCT Pub. Date: Apr. 6, 2023

(65) Prior Publication Data

US 2025/0135009 A1 May 1, 2025

(30) Foreign Application Priority Data

Oct. 1, 2021 (KR) ........................ 10-2021-0131088

(51) Int. Cl.

| | |
|---|---|
| ***A61K 47/36*** | (2006.01) |
| ***A61K 9/00*** | (2006.01) |
| ***A61K 9/06*** | (2006.01) |
| ***A61K 9/16*** | (2006.01) |
| ***A61K 31/573*** | (2006.01) |

(52) U.S. Cl.
CPC ............ *A61K 47/36* (2013.01); *A61K 9/0046* (2013.01); *A61K 9/06* (2013.01); *A61K 9/1652* (2013.01); *A61K 31/573* (2013.01)

(58) Field of Classification Search
CPC ........ A61K 47/36; A61K 9/0046; A61K 9/06; A61K 9/1652; A61K 31/573
See application file for complete search history.

(56) References Cited

U.S. PATENT DOCUMENTS

| | | | | |
|---|---|---|---|---|
| 8,445,465 B2 * | 5/2013 | Huh | C08L 5/08 | 536/20 |
| 9,066,855 B2 * | 6/2015 | Lichter | A61K 31/4535 | |
| 2007/0208134 A1 * | 9/2007 | Hunter | A61K 47/6957 | 525/54.1 |
| 2012/0277199 A1 | 11/2012 | Ye et al. | | |
| 2015/0291705 A1 * | 10/2015 | Huh | C08L 5/08 | 536/20 |
| 2016/0271148 A1 | 9/2016 | O'Malley et al. | | |

FOREIGN PATENT DOCUMENTS

| | | |
|---|---|---|
| JP | 2004-002329 A | 1/2004 |
| KR | 10-2012-0020386 A | 3/2012 |
| KR | 10-1477329 B1 | 12/2014 |

OTHER PUBLICATIONS

Cho et al., "Thermosensitive hexanoyl glycol chitosan based ocular delivery system for glaucoma therapy" in Acta Biomaterialia 39 (2016), 124-132. (Year: 2016).*
Cho, I. S. et al. "Thermosensitive hexanoyl glycol chitosan-based ocular delivery system for glaucoma therapy" Acta Biomaterialia (2016) 39, 124-132.
Shi, H. et al. "Thermosensitive glycol chitosan-based hydrogel as a topical ocular drug delivery system for enhanced ocular bioavailability" International Journal of Pharmaceutics (2019) 570, 118688.
Pierre, P. V. et al. "Middle ear administration of a particulate chitosan gel in an in vivo model of cisplatin ototoxicity" Frontiers in Cellular Neuroscience (2019) 13, 268.
International Search Report issued for PCT/KR2022/013938, dated Jan. 26, 2023.
Written Opinion of the International Searching Authority issued for PCT/KR2022/013938, dated Jan. 26, 2023.

* cited by examiner

*Primary Examiner* — Blessing M Fubara
(74) *Attorney, Agent, or Firm* — Westman, Champlin & Koehler, P.A.; Amanda M. Prose

(57) ABSTRACT

N-acylated glycol chitosan may be loaded with both a hydrophilic drug and a hydrophobic drug due to its amphiphilic nature, may have an increased intratympanic retention time by undergoing a sol-gel phase transition in the tympanic cavity, does not have any side effect, and may release a drug in an immediate or sustained release manner depending on the type and concentration of the drug, and thus it may be useful for intratympanic drug delivery and treatment of inner ear diseases.

7 Claims, 17 Drawing Sheets

[Fig. 1]
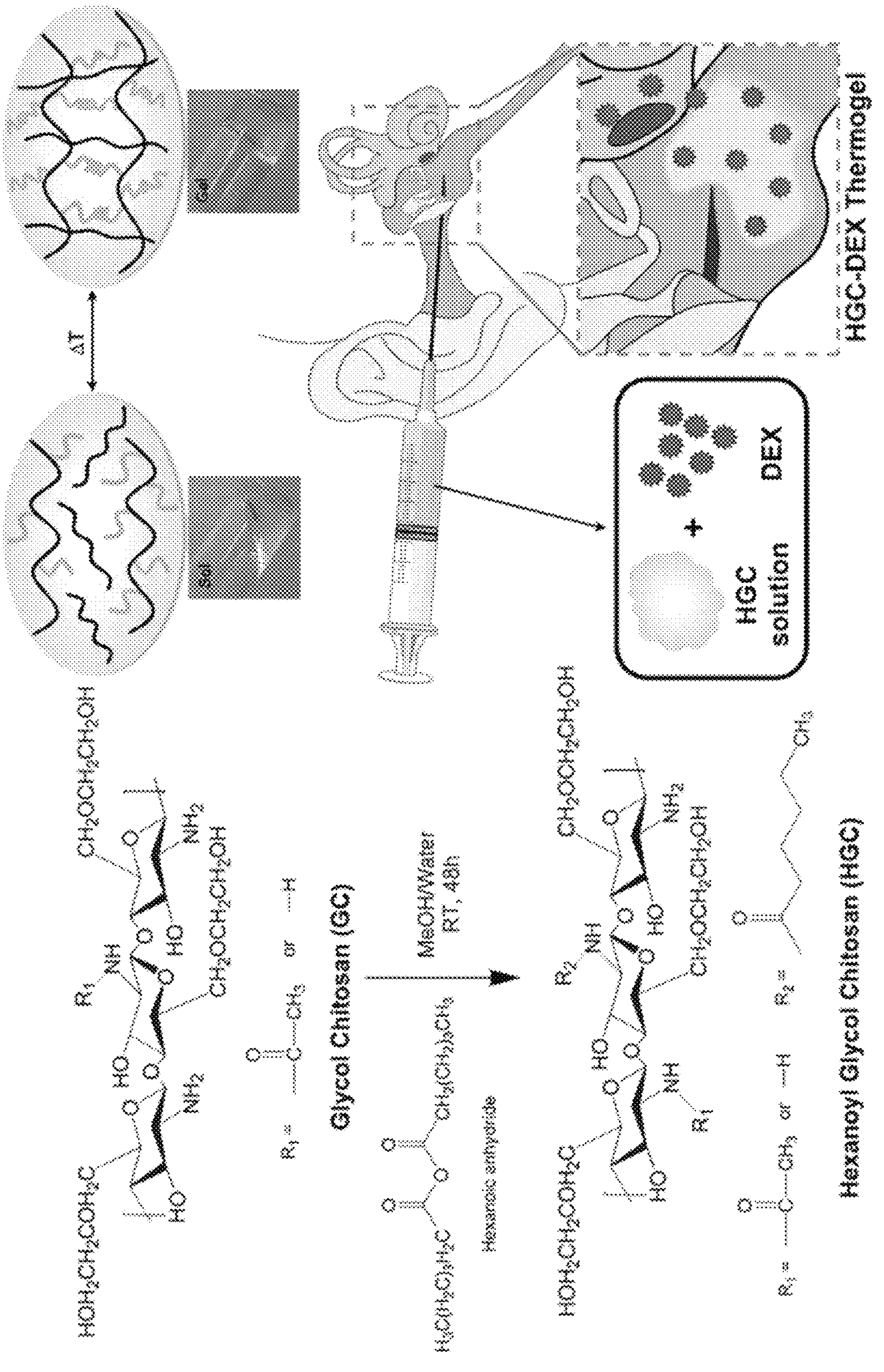

[Fig. 2a]
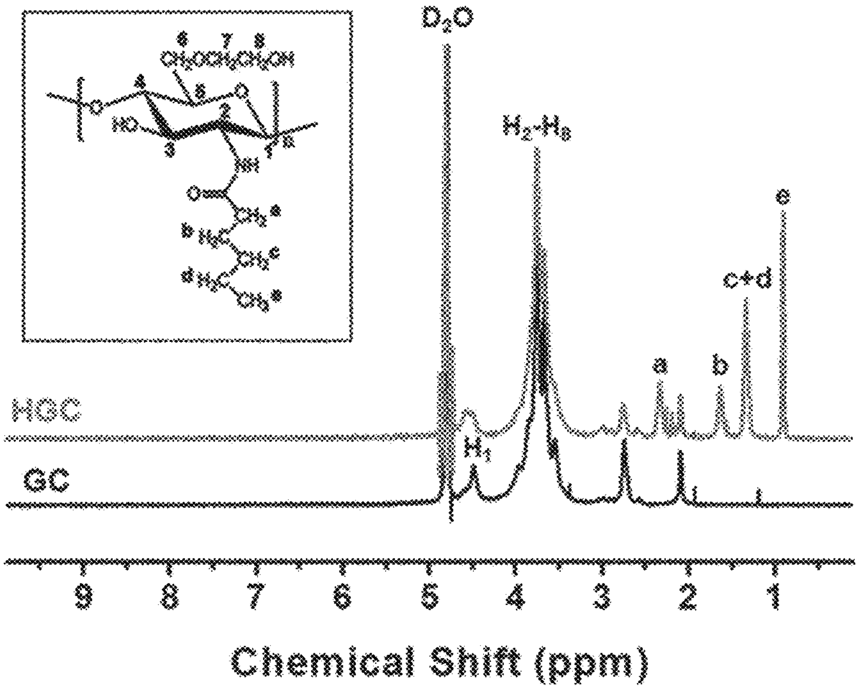
[Fig. 2b]
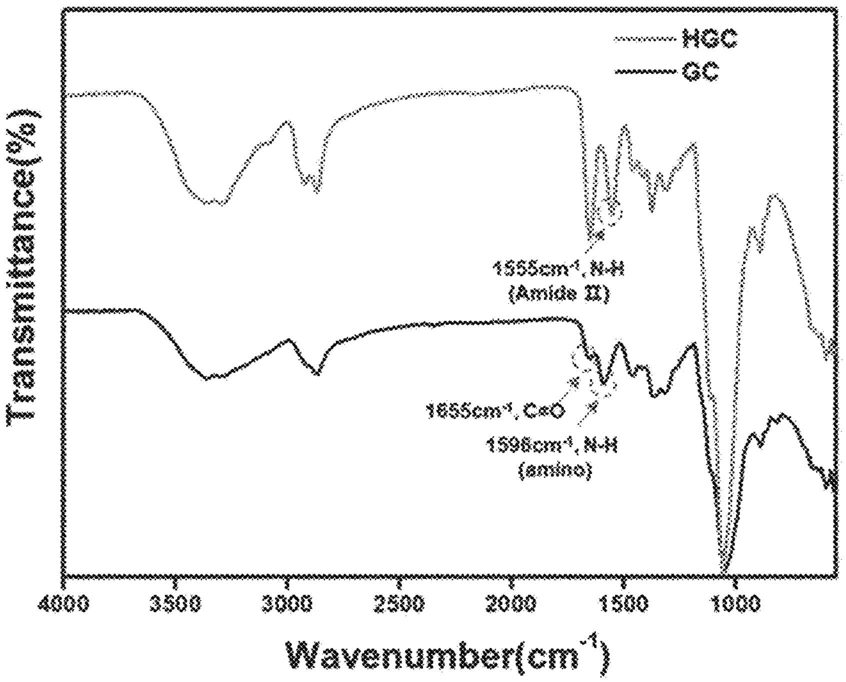

[Fig. 2c]
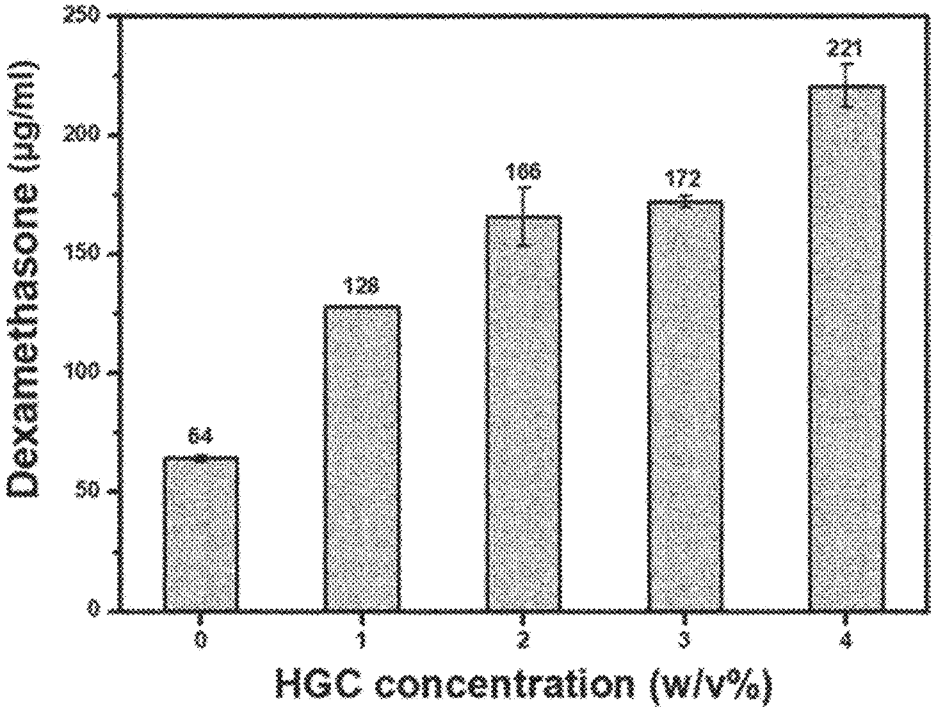

[Fig. 3a]
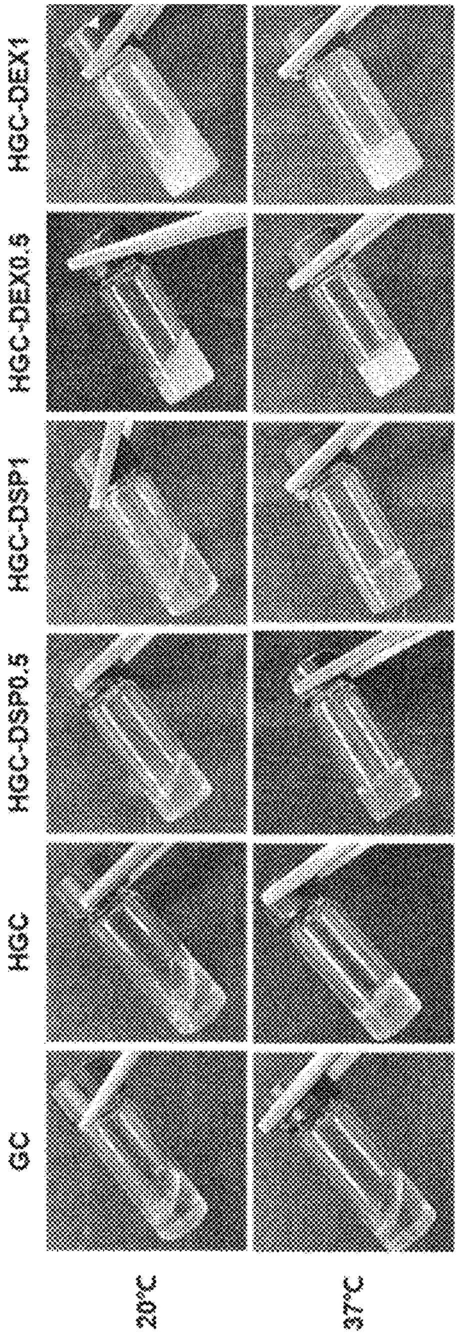

[Fig. 3b]
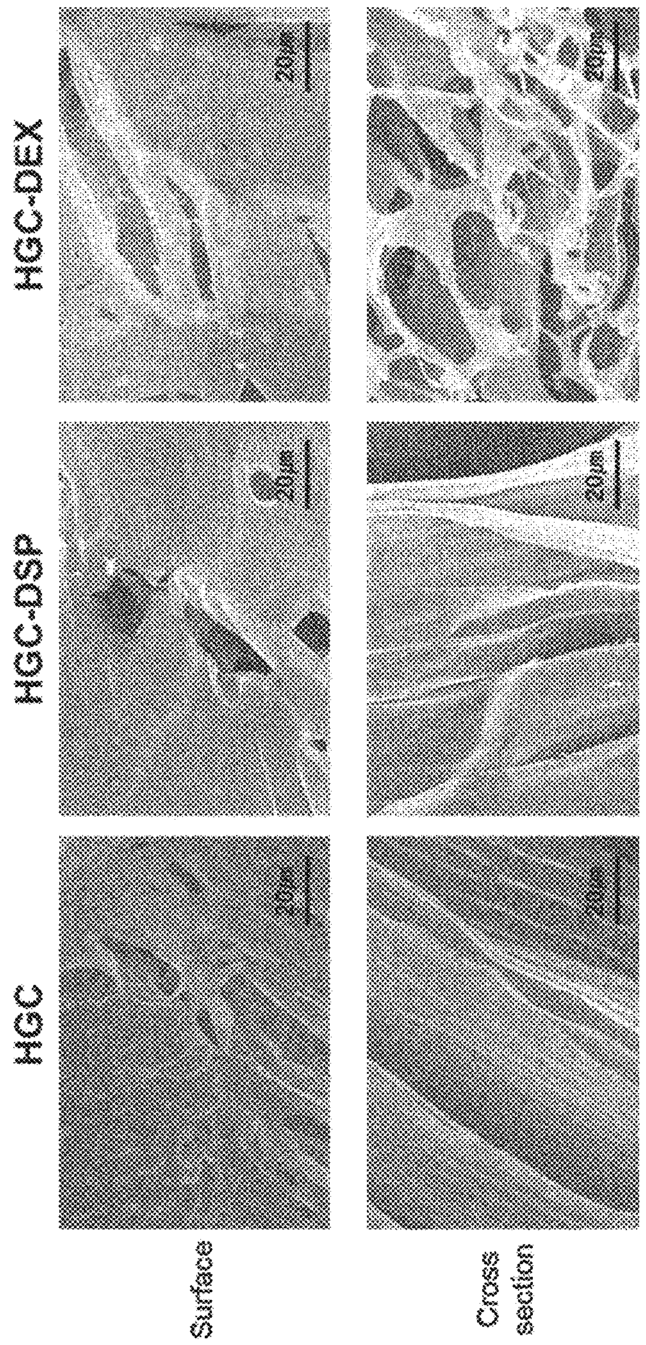

[Fig. 4a]
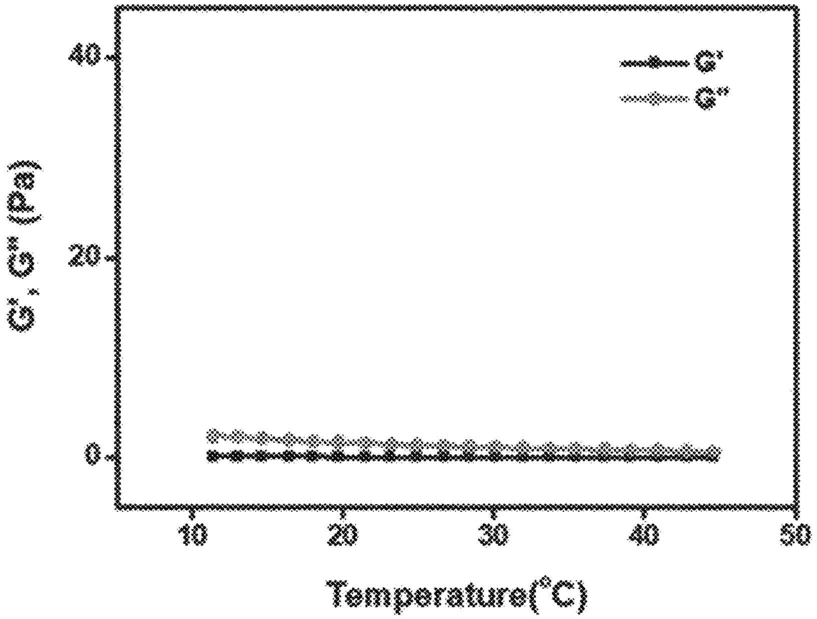
[Fig. 4b]
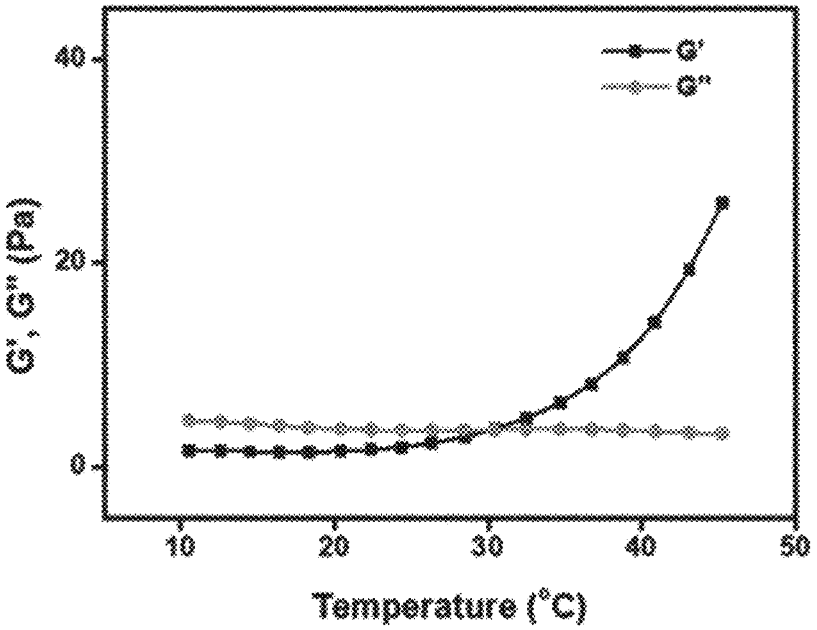

[Fig. 4c]
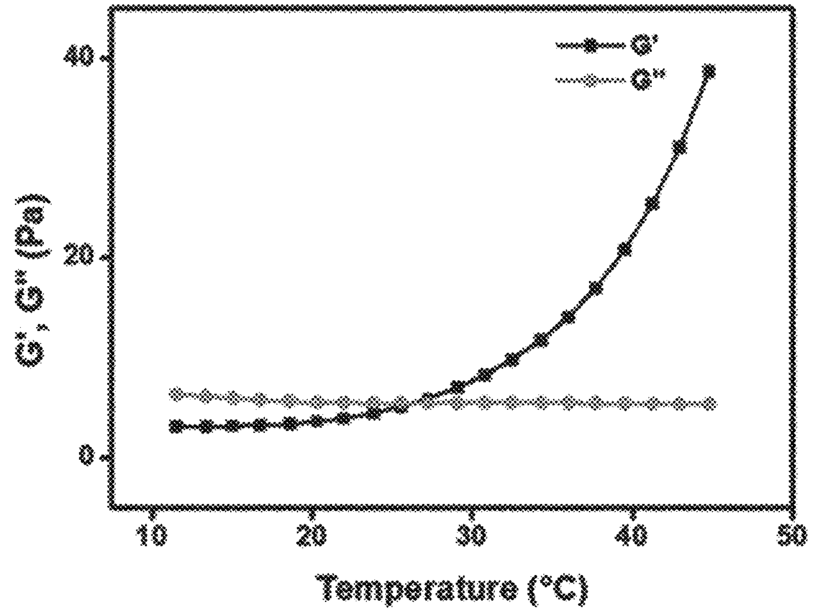
[Fig. 4d]
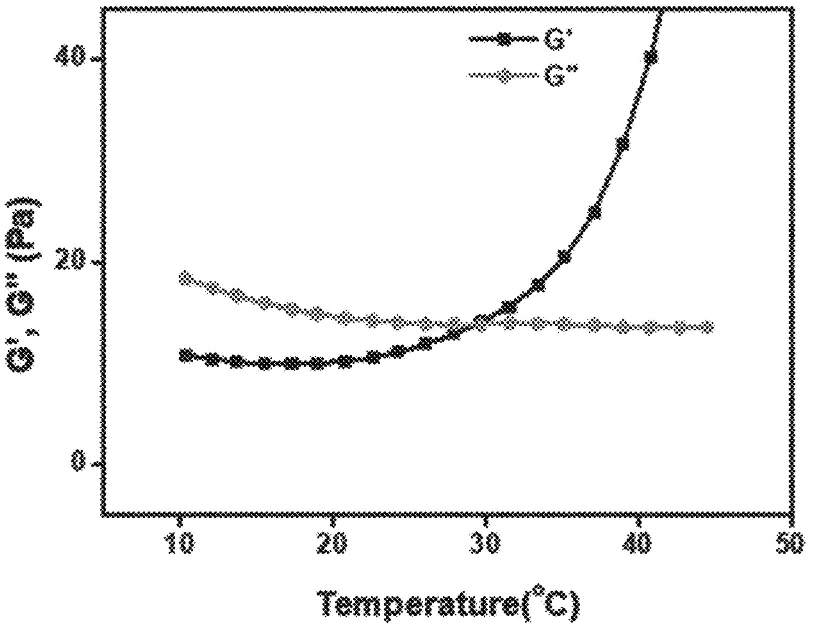

[Fig. 4e]
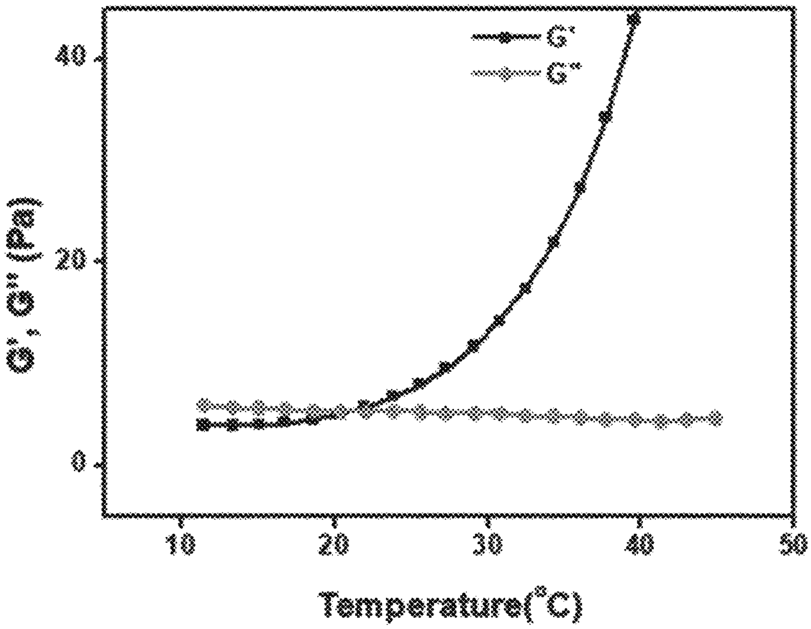
[Fig. 4f]
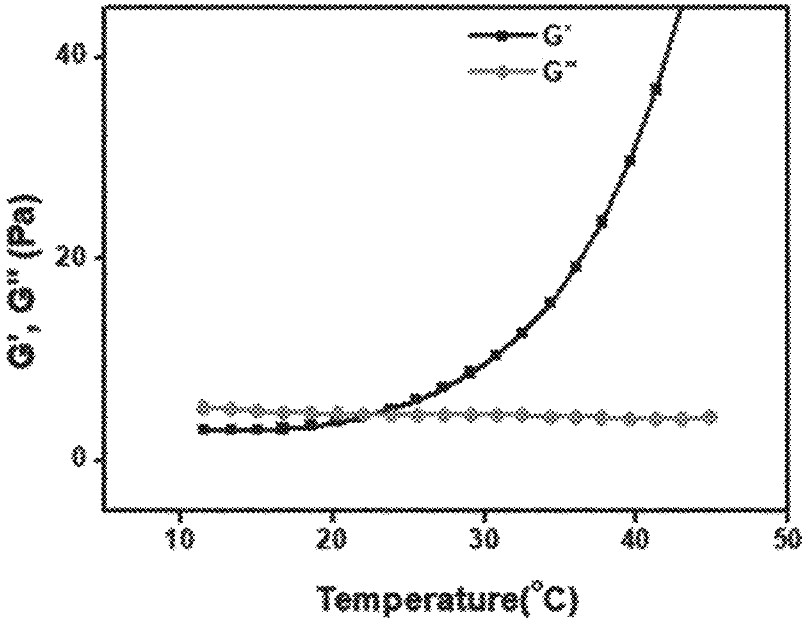

[Fig. 5a]
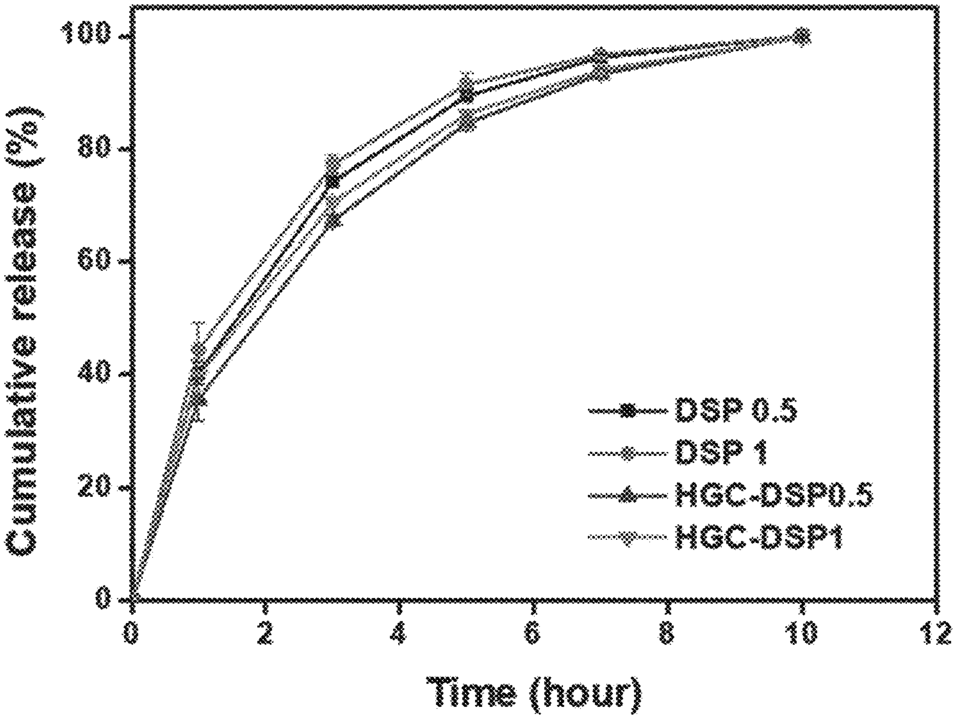
[Fig. 5b]
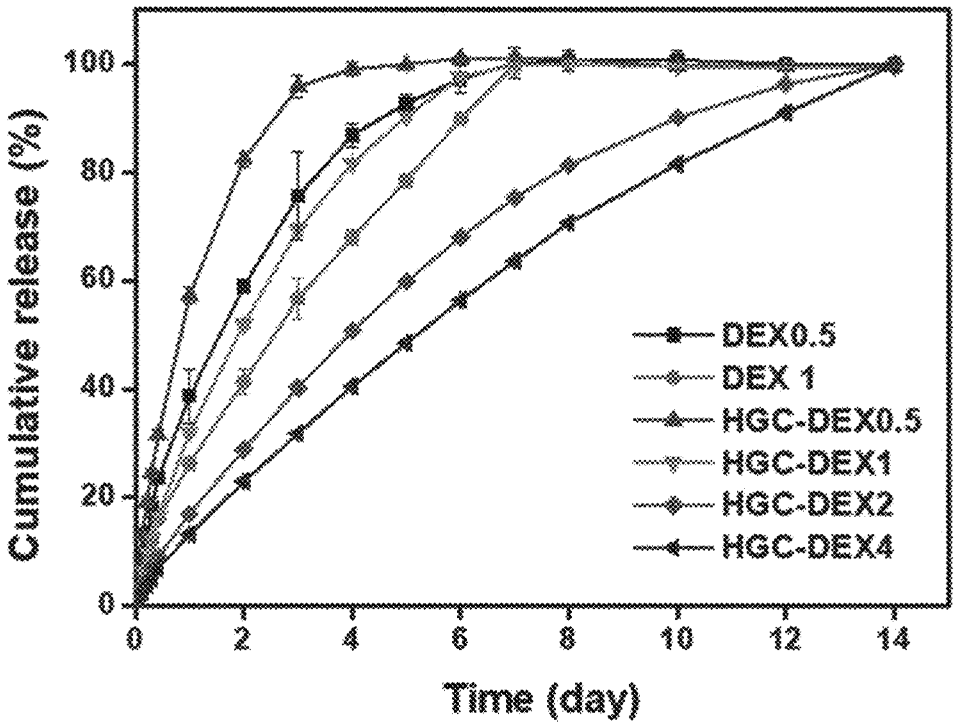

[Fig. 6]
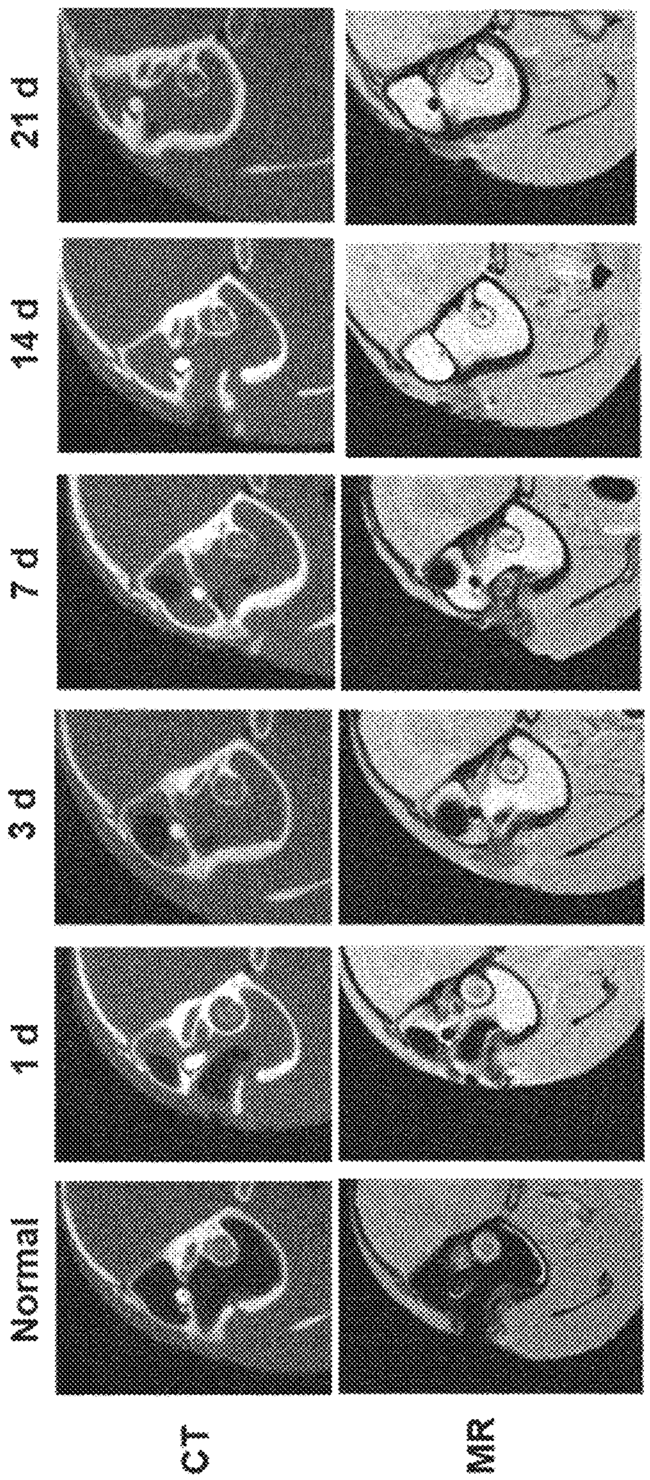

[Fig. 7a]
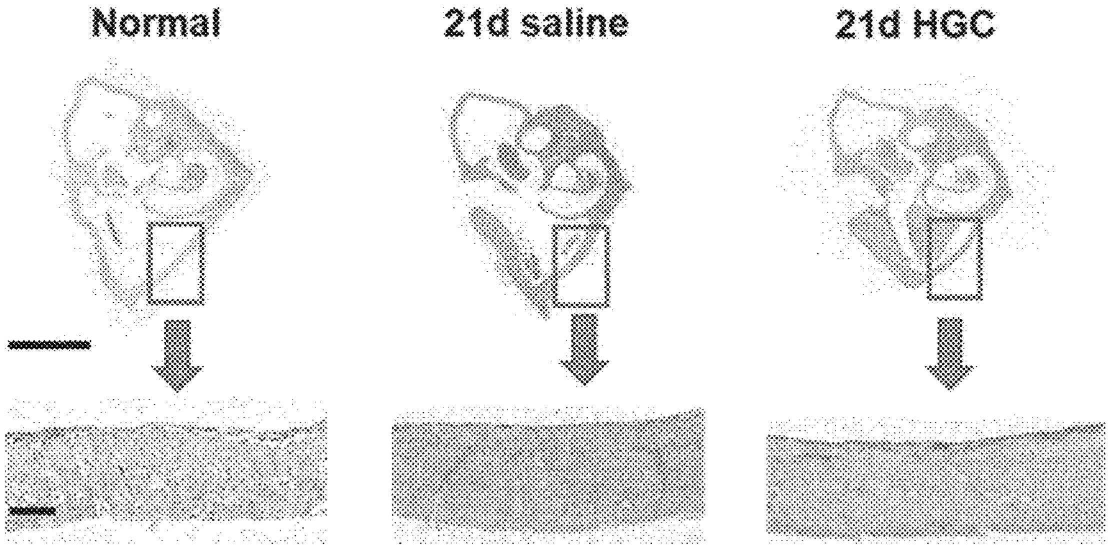
[Fig. 7b]
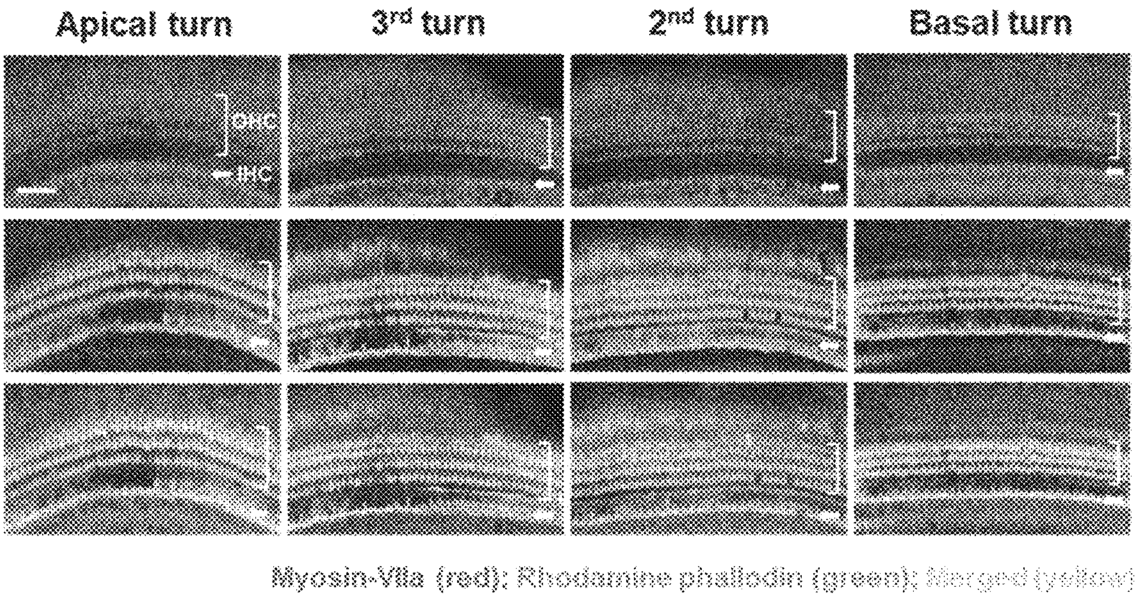

[Fig. 8a]
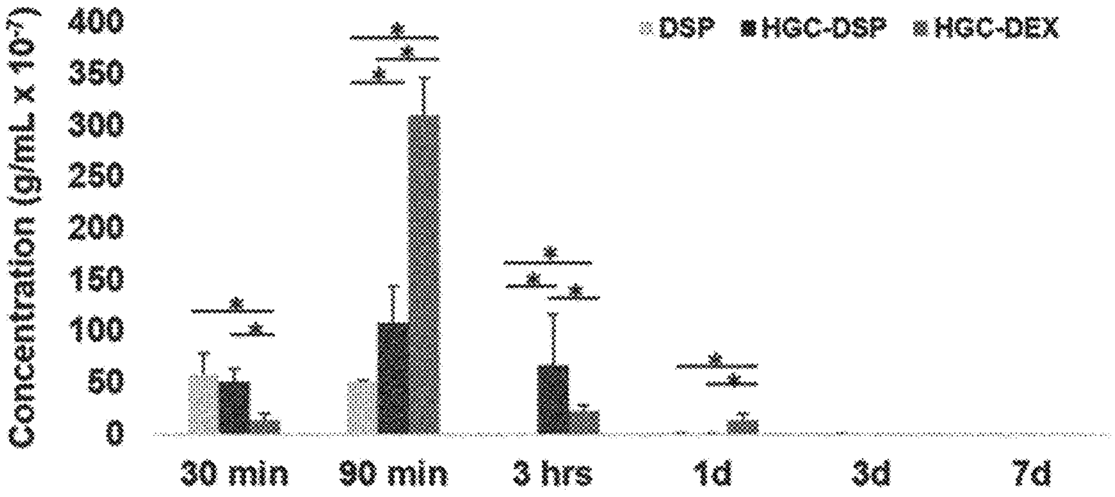
[Fig. 8b]
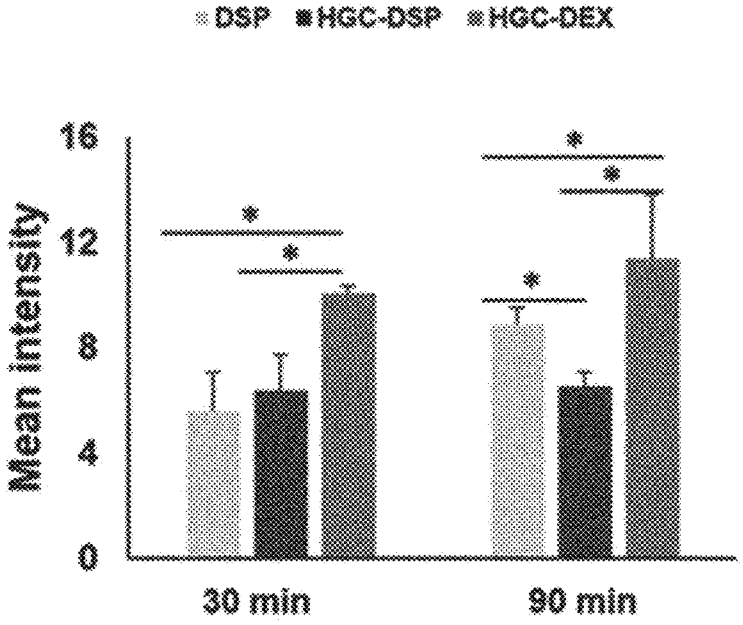

[Fig. 9a]
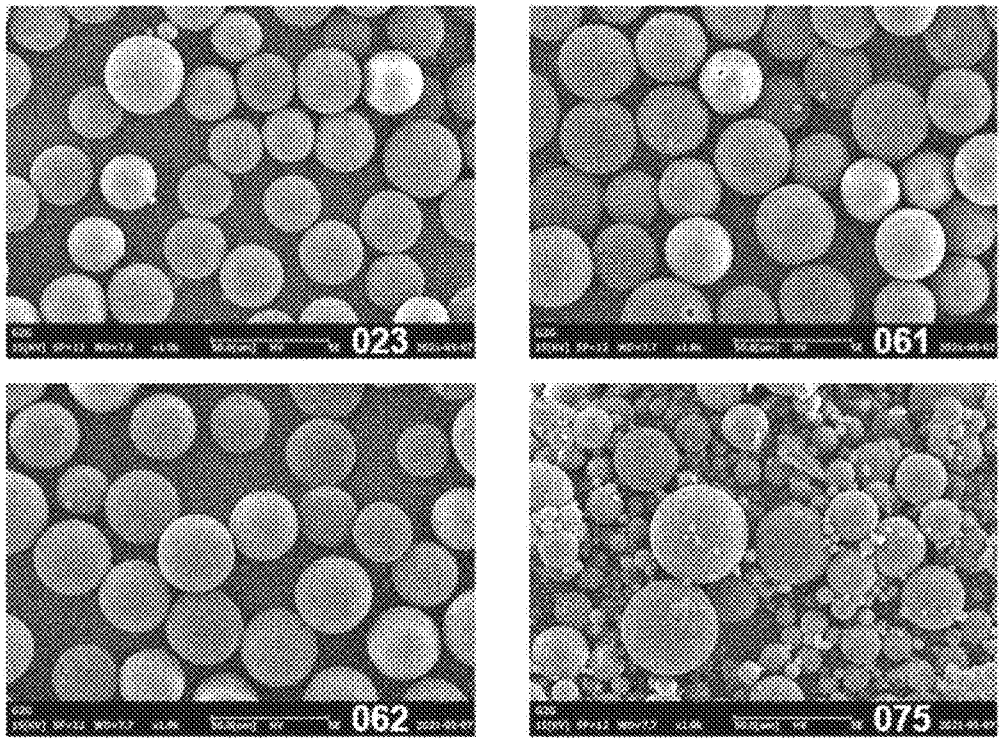
[Fig. 9b]
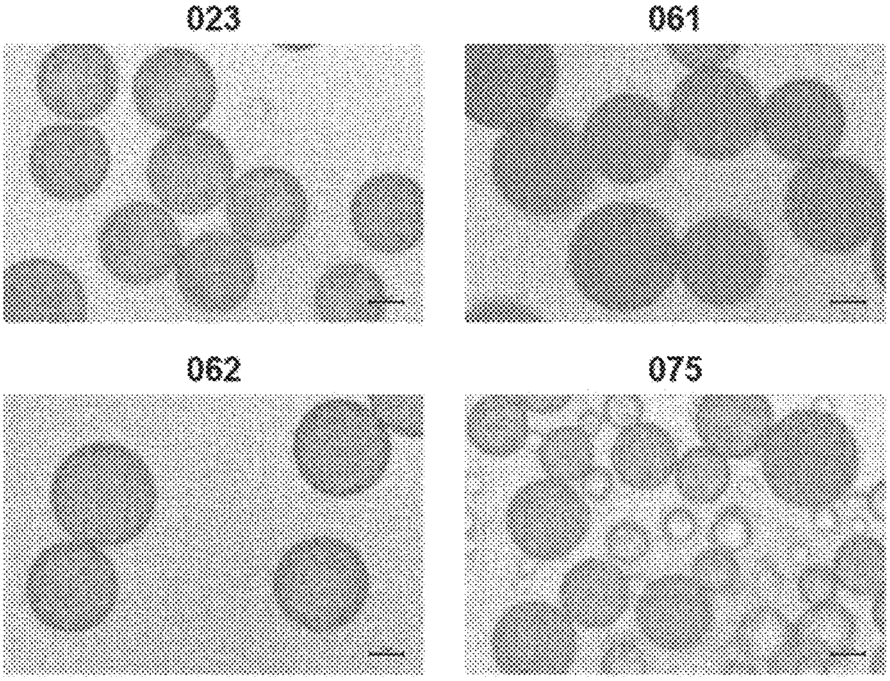

[Fig. 10a]
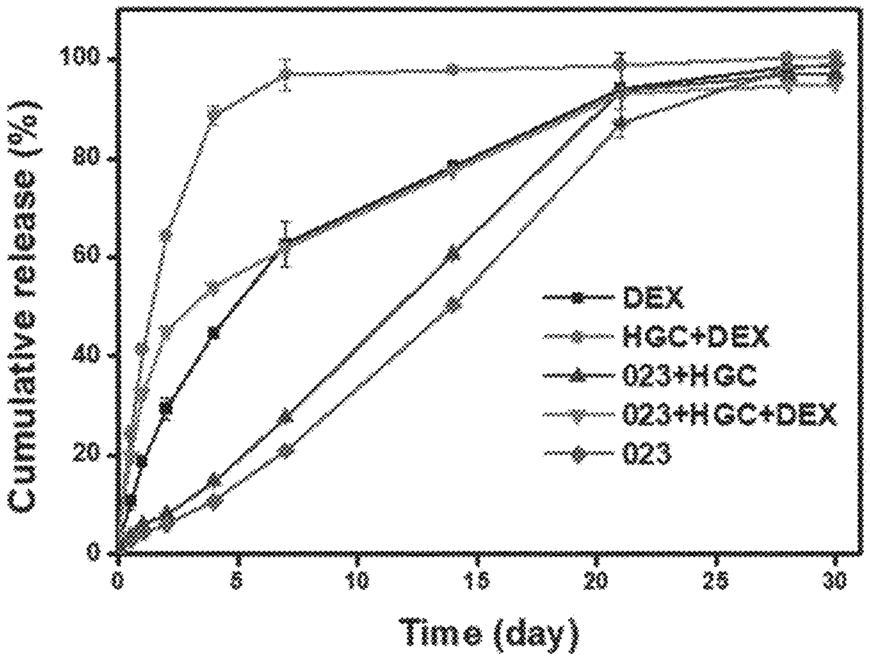
[Fig. 10b]
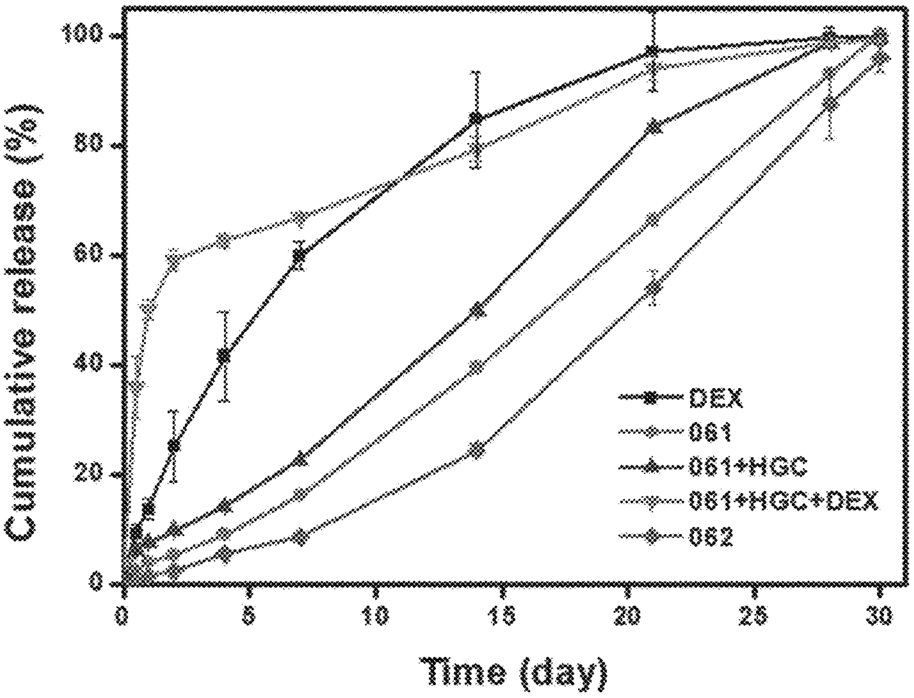

[Fig. 11]
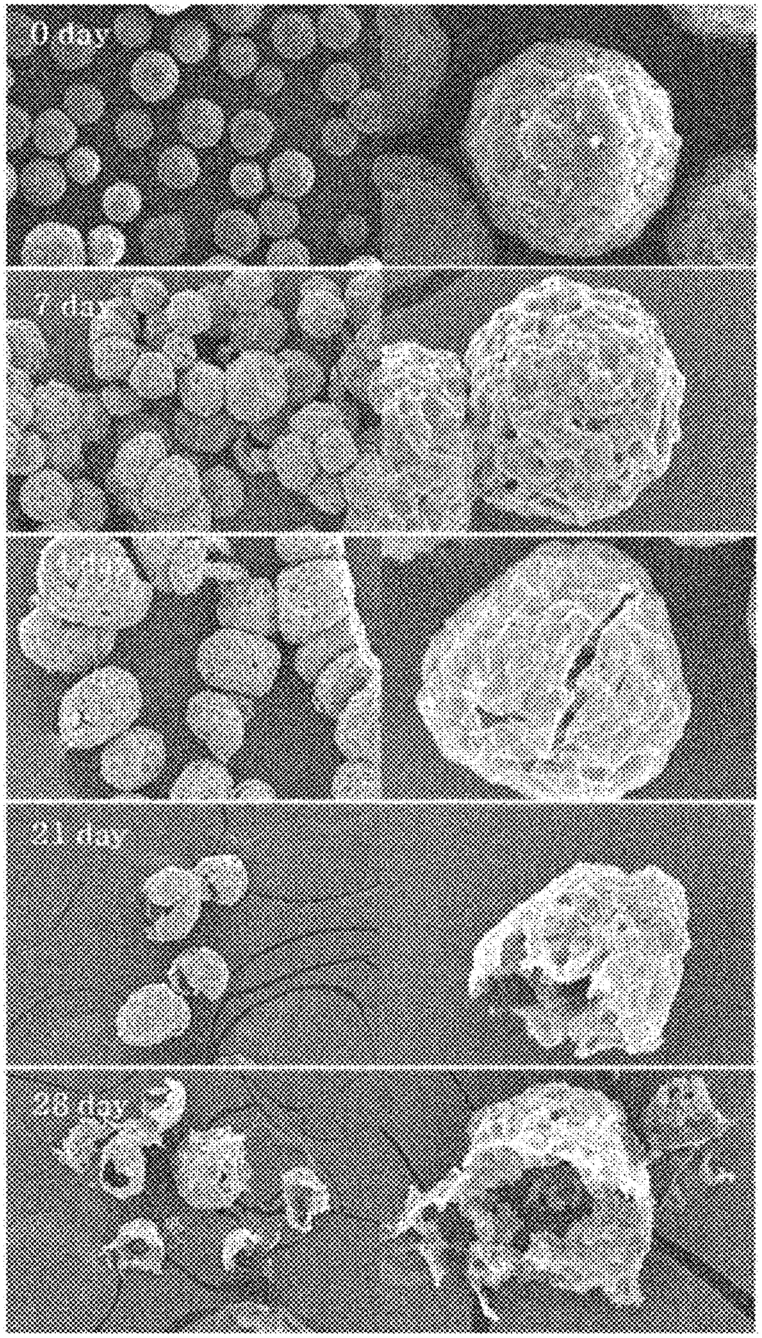

[Fig. 12]
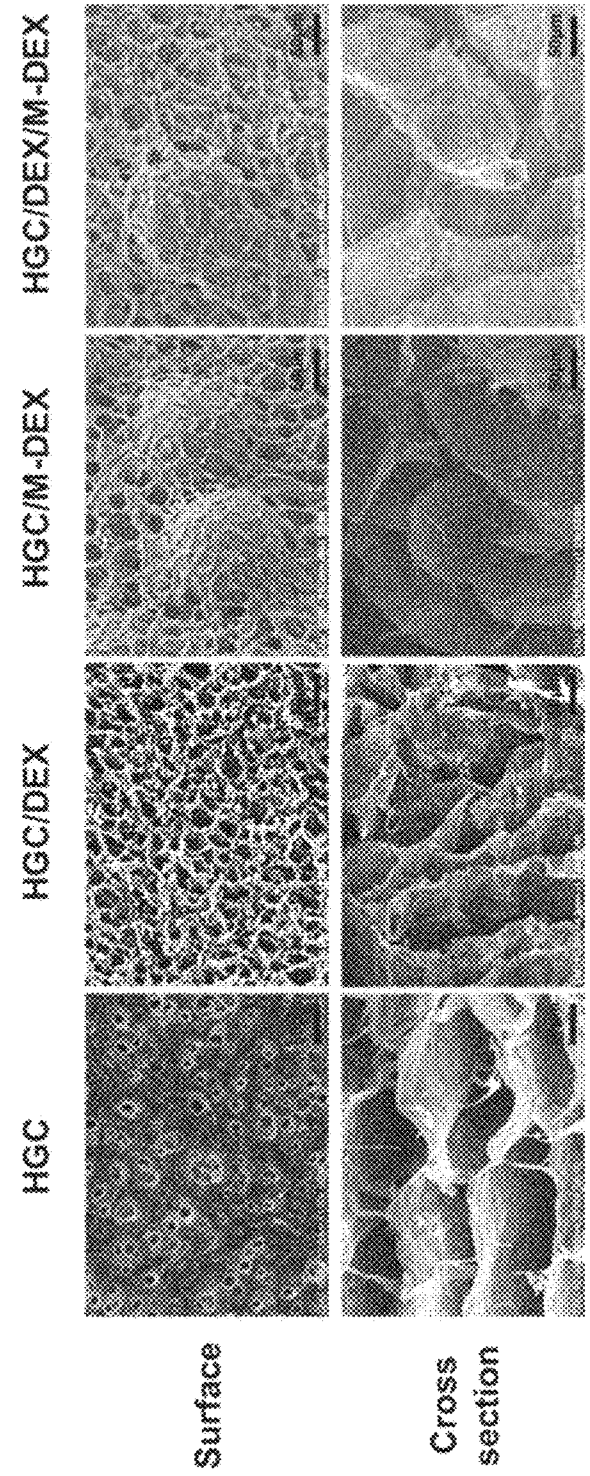

[Fig. 13]
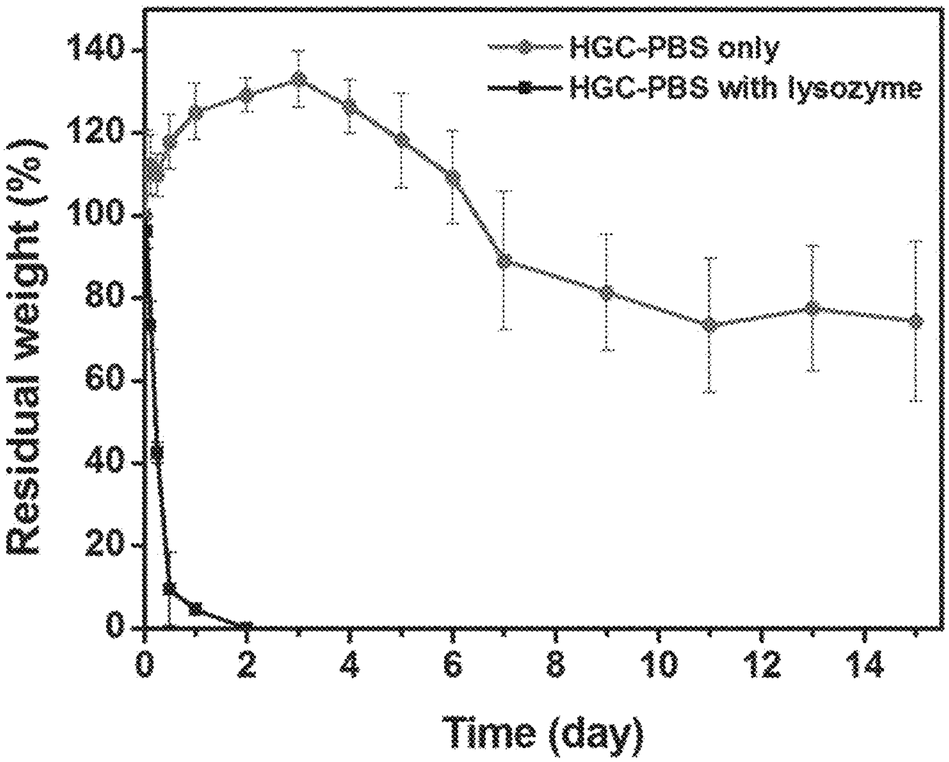

INTRATYMPANIC DRUG CONTROLLED RELEASE-TYPE FORMULATION COMPRISING N-ACYLATED GLYCOL CHITOSAN

CROSS-REFERENCE TO RELATED APPLICATION

This Application is a Section 371 National Stage Application of International Application No. PCT/KR2022/013938, filed Sep. 19, 2022 and published as WO 2023/054951 A1 on Apr. 6, 2023, in Korean, which claims priority to KR Patent Application No. 10-2021-0131088 filed Oct. 1, 2021, the contents of which are hereby incorporated by reference in their entirety.

TECHNICAL FIELD

This application claims priority based on Korean Patent Application No. 10-2021-0131088, filed on Oct. 1, 2021.

The present invention relates to an intratympanic controlled drug release formulation comprising N-acylated glycol chitosan.

BACKGROUND ART

When a drug for treating inner ear disease is administered systemically, drug delivery to the inner ear is not efficient due to the blood-labyrinthine barrier. In addition, systemic drug administration at high doses to achieve and maintain drug concentrations in the inner ear is accompanied by toxicity and side effects. Thus, local administration is efficient for drug delivery to the inner ear.

Intratympanic administration refers to the administration of a drug by injection into a space called the middle ear cavity or tympanic cavity, and is a widely used method for local administration to the inner ear. Intratympanic administration delivers drugs to the inner ear more efficiently and has fewer side effects than systemic administration.

Drugs administered intratympanically are delivered by diffusion to the inner ear through the round window membrane (RWM). Thus, in order to efficiently deliver a drug to the inner ear, the drug must be in contact with the round window membrane at a high concentration for a long time. However, since a drug located in the middle ear cavity by intratympanic administration is easily discharged to the outside through the Eustachian tube, it is difficult to contact the round window membrane at a high concentration for a long time. Therefore, prolonging drug retention in the middle ear cavity is considered an approach to enhance drug delivery to the inner ear.

Thermogel, which exhibits thermo-reversible sol-gel transition properties, can be injected in a sol state and forms a gel in the body, and thus it is suitable for intratympanic drug delivery. Thermogel in a sol state may be mixed with a drug and loaded with the drug. When thermogel mixed with a drug is injected, it is solidified into a gel in response to body temperature. Poloxamers, representative thermogels, have been used for drug delivery to the inner ear. However, poloxamers require a high concentration (more than 20 wt %) for effective thermogelation, and are not sufficiently biodegradable and physically stable, and side effects thereof have been reported.

Glycol chitosan (GC), a water-soluble derivative of chitosan, has promising properties as a biomaterial, including high biocompatibility, biodegradability, and water solubility at neutral pH (Korean Patent Application Publication No.

10-2012-0020386 (Mar. 8, 2012). However, it is not known whether intratympanic administration of a mixture of N-acyl glycol chitosan and a drug enables efficient drug delivery to the inner ear and is accompanied by side effects.

DISCLOSURE

Technical Problem

According to one embodiment, there is provided a pharmaceutical composition for intratympanic administration for treating inner ear disease comprising N-acylated glycol chitosan.

According to another embodiment, there is provided a formulation for intratympanic administration comprising N-acylated glycol chitosan.

Technical Solution

One aspect provides a pharmaceutical composition for treating inner ear disease by administration through intratympanic injection, comprising a polymer having a unit represented by Formula 1 below, and a drug for treating inner ear disease, wherein the polymer undergoes a sol-gel phase transition depending on temperature:

[Formula 1]

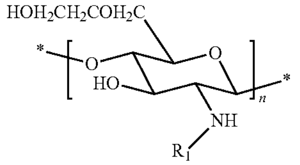

In Formula 1 above, $R_1$ is H or an acyl group having 1 to 10, 1 to 9, 1 to 8, 1 to 7, or 1 to 6 carbon atoms, and n is 10 to 10,000, 10 to 9,500, 10 to 9,000, 10 to 8,500, 10 to 8,000, 10 to 7,500, 10 to 7,000, 10 to 6,500, 10 to 6,000, 10 to 5,500, 10 to 5,000, 10 to 4,500, 10 to 4,000, 10 to 3,500, 10 to 3,000, 10 to 2,500, 10 to 2,000, 10 to 1,500, 10 to 1,000, 10 to 900, 10 to 800, 10 to 700, 10 to 600, or 10 to 500.

The acyl group may be (—(C═O)-alkyl group), and the alkyl group in the acyl group may have 1 to 10, 1 to 9, 1 to 8, 1 to 7, or 1 to 6 carbon atoms, and may be a straight or branched chain group.

According to one embodiment, the polymer is in the state of sol that can be administered by injection at room temperature, and it may be a thermogel that undergoes a phase transition to a gel in response to body temperature when administered intratympanically. The polymer is a drug carrier that can be loaded with a drug, and when the polymer and the drug are mixed together and administered intratympanically, the mixture undergoes a phase transition to a drug-loaded gel. The gelled pharmaceutical composition may have an increased residence time in the middle ear cavity, and thus may increase the contact time between the drug and the round window membrane and continuously deliver the drug to the inner ear. According to one example, it was confirmed that, when the pharmaceutical composition was administered intratympanically, side effects such as inflammatory responses and loss of auditory hair cells did not occur, indicating that the pharmaceutical composition is highly safe. Such safety was not previously known.

According to one embodiment, the polymer contains a hydrophilic glycol chitosan backbone and a hydrophobic acyl group (e.g., hexanoyl group), and thus it can be loaded with both hydrophilic and hydrophobic drugs.

According to one embodiment, $R_1$ may be H, an acetyl group, or a hexanoyl group.

According to one embodiment, the polymer may have a degree of polymerization (DP) of 150 to 400, 150 to 350, 150 to 300, 150 to 250, 200 to 400, 200 to 350, 200 to 300, or 200 to 250.

According to one embodiment, the temperature at which the sol-gel phase transition occurs may be 30 to 34 °C, 30 to 33 °C, 30 to 32 °C, 31 to 34 °C, 31 to 33 °C, 31 to 32 °C, 32 to 34 °C, or 32 to 33 °C.

According to one embodiment, the polymer may be a polymer comprising 8 to 10% of N-acetylated glycol chitosan units, 30 to 40% of N-hexanoylated glycol chitosan units, and the balance of glycol chitosan units.

According to one embodiment, the polymer may be a compound having a unit represented by Formula 2 below:

The pharmaceutical composition may comprise the polymer in an amount of 0.5 to 4 wt %, 0.6 to 4 wt %, 0.7 to 4 wt %, 0.8 to 4 wt %, 0.9 to 4 wt %, or 1 to 4 wt %.

The pharmaceutical composition may remain in the tympanic cavity for at least 30 minutes, at least 90 minutes, at least 3 hours, at least 1 day, at least 2 days, at least 3 days, at least 4 days, at least 5 days, at least 6 days, at least 7 days, at least 8 days, at least 9 days, at least 10 days, at least 11 days, or at least 12 days.

According to one embodiment, the pharmaceutical composition may release a hydrophilic drug in an immediate release manner and release a hydrophobic drug in a sustained release manner, in the tympanic cavity.

The immediate release refers to the property of releasing the drug immediately after administration so that the initial effect of the drug appears quickly, and the sustained release refers to the property of releasing the drug slowly and continuously so that the therapeutically effective amount or effective concentration of the drug may be maintained for a long period of time. The therapeutically effective amount refers to an amount effective for ameliorating or reducing hearing loss in the subject being treated, and may vary depending on the severity of the subject, the drug administered, and the method of administration.

[Formula 2]

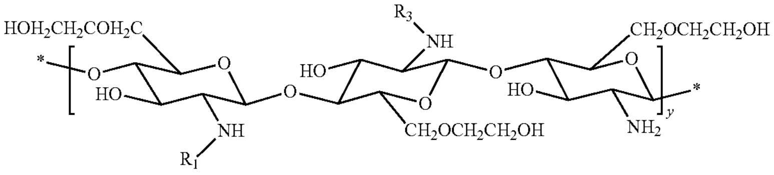

In Formula 2 above, $R_2$ may be H or an acetyl group ($—CO—CH_3$), $R_3$ may be a hexanoyl group ($—CO—CH_2CH_2CH_2CH_2CH_3$), and y may be 10 to 10,000, 10 to 9,500, 10 to 9,000, 10 to 8,500, 10 to 8,000, 10 to 7,500, 10 to 7,000, 10 to 6,500, 10 to 6,000, 10 to 5,500, 10 to 5,000, 10 to 4,500, 10 to 4,000, 10 to 3,500, 10 to 3,000, 10 to 2,500, 10 to 2,000, 10 to 1,500, 10 to 1,000, 10 to 900, 10 to 800, 10 to 700, 10 to 600, or 10 to 500.

According to one embodiment, the drug for treating inner ear disease may be a corticosteroid-based drug.

The corticosteroid-based drug may be, for example, clobetasol, halometasone, dexamethasone, diflorasone, fluocinonide, halobetasol, amcinonide, halcinonide, hydrocortisone, fluticasone, mometasone, fluocinolone, desonide, prednisone, methylprednisolone, prednisolone, a hydrate or solvate thereof, or a combination thereof. According to one example, it may be dexamethasone, dexamethasone phosphate, or a pharmaceutically acceptable salt thereof.

The drug for treating inner ear disease may be dispersed in the polymer.

According to one embodiment, the drug for treating inner ear disease may be the drug itself, a form in which the drug is dispersed in microspheres, or a combination thereof. The composition may be in a form wherein microspheres having the drug dispersed therein and the polymer are mixed and dispersed, or a form wherein microspheres having the drug dispersed therein, the drug itself, and the polymer are mixed and dispersed. The microspheres are fine particles composed of a biocompatible and biodegradable polymer, and are well known in the field of drug delivery technology. The material forming the microsphere is not particularly limited as long as it is a polymer having excellent biocompatibility and biodegradability. For example, the biocompatible polymer may be PLGA, PEG, PLA, PGA, PHA, a copolymer thereof, or a combination thereof. The microspheres may be composed of a biodegradable polymer having a molecular weight of 5,000 to 200,000. The diameter of the microsphere may be 10 to 100 μm.

The mixing ratio of the polymer to the drug may be, based on parts by weight, 4:0.5 to 4:4, 4:1 to 4:4, 4:1.5 to 4:4, 4:2 to 4:4, 4:2.5 to 4:4, 4:3 to 4:4, 4:3.5 to 4:4, 4:0.5 to 4:3.5, 4:1 to 4:3.5, 4:1.5 to 4:3.5, 4:2 to 4:3.5, 4:2.5 to 4:3.5, 4:3 to 4:3.5, 4:0.5 to 4:3, 4:1 to 4:3, 4:1.5 to 4:3, 4:2 to 4:3, 4:2.5 to 4:3, 4:0.5 to 4:2.5, 4:1 to 4:2.5, 4:1.5 to 4:2.5, 4:2 to 4:2.5, 4:0.5 to 4:2, 4:1 to 4:2, 4:1.5 to 4:2, 4:0.5 to 4:1.5, 4:1 to 4:1.5, or 4:0.5 to 4:1.

The content of the drug may be 0.5 to 4 wt %, 1 to 4 wt %, 1.5 to 4 wt %, 2 to 4 wt %, 2.5 to 4 wt %, 3 to 4 wt %, 3.5 to 4 wt %, 0.5 to 3.5 wt %, 1 to 3.5 wt %, 1.5 to 3.5 wt %, 2 to 3.5 wt %, 2.5 to 3.5 wt %, 3 to 3.5 wt %, 0.5 to 3 wt %, 1 to 3 wt %, 1.5 to 3 wt %, 2 to 3 wt %, 2.5 to 3 wt %, 0.5 to 2.5 wt %, 1 to 2.5 wt %, 1.5 to 2.5 wt %, 2 to 2.5 wt %, 0.5 to 2 wt %, 1 to 2 wt %, 1.5 to 2 wt %, 0.5 to 1.5 wt %, 1 to 1.5 wt %, or 0.5 to 1 wt %.

The pharmaceutical composition may release the drug continuously for at least 30 minutes, at least 90 minutes, at least 3 hours, at least 1 day, at least 2 days, at least 3 days, at least 4 days, at least 5 days, at least 6 days, at least 7 days, at least 8 days, at least 9 days, at least 10 days, at least 11 days, or at least 12 days.

According to one embodiment, the pharmaceutical composition may release the drug in an immediate or sustained release manner depending on the concentration of the drug contained therein. Specifically, the pharmaceutical composition may release the drug in a sustained release manner when the concentration of the drug contained therein is 1.5 to 4 wt %, 1.6 to 4 wt %, 1.7 to 4 wt %, 1,8 to 4 wt %, 1.9 to 4 wt %, or 2 to 4 wt %, and may release the drug in an immediate release manner when the concentration of the drug is lower than the lower limit of the above range.

Referring to the results of an in vitro drug release experiment in one example, a pharmaceutical composition containing 0.5 wt % or 1 wt % of the drug released the drug in vitro in an immediate release manner, and a pharmaceutical composition containing 2 wt % or 4 wt % of the drug released the drug in vitro in a sustained release manner for up to 14 days (see FIG. 5). In addition, referring to the results of an animal test in one example, when a pharmaceutical composition containing 0.5 wt % of the drug was administered intratympanically, it released the drug continuously for 1 day. Therefore, it is expected that a pharmaceutical composition containing the drug at a higher concentration will release the drug in the tympanic cavity in a sustained release manner so that the release period of the drug will be prolonged (see FIG. 8)

The inner ear disease may be, for example, Meniere's disease; sensorineural hearing loss; ototoxic hearing loss caused by drugs such as antipyretics, anticancer drugs, and antibiotics; noise-induced hearing loss; age-related heating loss; tinnitus; vestibular neuritis; auditory nerve tumor; osteosclerosis; traumatic hearing loss caused by perilymph fistula, labyrinth concussion, and temporal bone fracture; or autoimmune inner ear disease. The autoimmune inner ear disease may be caused by ankylosing spondylitis, systemic lupus erythematosus (SLE), Sjögren's syndrome, Cogan's disease, ulcerative colitis, Wegener's granulomatosis, rheumatoid arthritis, scleroderma, or Behcet's disease.

The intratympanic administration may also be referred to as administration into the tympanum, and is a method of injecting the composition into the middle ear or inner ear behind the tympanum. The intratympanic administration may be administering the composition to the middle ear so that the composition can come into contact with the round window membrane. The intratympanic administration may be performed using a syringe, a pump, a microinjection device, a sponge material, or the like. The dosage of the composition may vary depending on the patient's condition and body weight, the severity of the disease, the form of the drug, and the route and duration of administration, and may be appropriately selected by a person skilled in the art.

The pharmaceutical composition may further comprise a Na/K ATPase modulator, chemotherapeutic agent, collagen, gamma-globulin, interferon, antibacterial agent, antibiotic, local acting anesthetic, platelet activating factor antagonist, ear protector, nitric oxide synthase inhibitor, vertigo inhibitor, vasopressin antagonist, antiviral agent, antiemetic, anti-TNF agent, vasopressin receptor modulator, methotrexate, cyclophosphamide, immunosuppressant, macrolide, latanoprost, TNF converting enzyme inhibitor, IKK inhibitor, glutamate receptor modulator, anti-apoptotic agent, neuroprotectant, thalidomide, c-jun inhibitor compound, hyaluronidase, antioxidant, IL-1 beta modulator, ERR-beta antagonist, IGF-modulator, Toll-like receptor, KCNQ channel modulator, neurotrophin modulator, ATOH modulator, or a combination thereof.

The pharmaceutical composition may further comprise carriers, excipients, and diluents, which are commonly used in the manufacture of medicaments. The pharmaceutical composition may be formulated and used in the form of oral dosage forms such as powders, granules, tablets, capsules, suspensions, emulsions, syrups, and aerosols, as well as external preparations, suppositories, and sterile injectable solutions. Carriers, excipients, and diluents that may be included in the composition include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil, without being particularly limited thereto.

Another aspect provides an intratympanic controlled drug release formulation comprising a polymer having a unit represented by Formula 1 below, and a drug for treating inner ear disease dispersed in the polymer, wherein the formulation undergoes a sol-gel phase transition after intratympanic injection thereof:

[Formula 1]

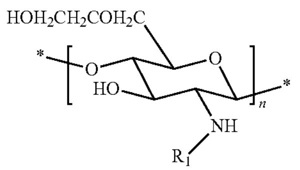

In Formula 1 above, $R_1$ is H or an acyl group having 1 to 10, 1 to 9, 1 to 8, 1 to 7, or 1 to 6 carbon atoms, and n is 10 to 10,000, 10 to 9,500, 10 to 9,000, 10 to 8,500, 10 to 8,000, 10 to 7,500, 10 to 7,000, 10 to 6,500, 10 to 6,000, 10 to 5,500, 10 to 5,000, 10 to 4,500, 10 to 4,000, 10 to 3,500, 10 to 3,000, 10 to 2,500, 10 to 2,000, 10 to 1,500, 10 to 1,000, 10 to 900, 10 to 800, 10 to 700, 10 to 600, or 10 to 500.

The acyl group may be (—(C═O)-alkyl group), and the alkyl group in the acyl group may have 1 to 10, 1 to 9, 1 to 8, 1 to 7, or 1 to 6 carbon atoms, and may be a straight or branched chain group.

The controlled drug release refers to controlling the release rate and delivery rate of the drug in the tympanic cavity.

According to one embodiment, $R_1$ may be H, an acetyl group, or a hexanoyl group.

According to one embodiment, the polymer may have a degree of polymerization (DP) of 150 to 400, 150 to 350, 150 to 300, 150 to 250, 200 to 400, 200 to 350, 200 to 300, or 200 to 250.

According to one embodiment, the temperature at which the sol-gel phase transition occurs may be 30 to 34 °C, 30 to 33 °C, 30 to 32 °C, 31 to 34 °C, 31 to 33 °C, 31 to 32 °C, 32 to 34 °C, or 32 to 33 °C.

According to one embodiment, the polymer may be a polymer comprising 8 to 10% of N-acetylated glycol chitosan units, 30 to 40% of N-hexanoylated glycol chitosan units, and the balance of glycol chitosan units.

According to one embodiment, the polymer may be a compound having a unit represented by Formula 2 below:

[Formula 2]

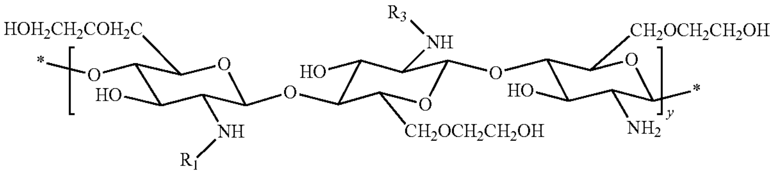

In Formula 2 above, $R_2$ may be H or an acetyl group (—CO—$CH_3$), $R_3$ may be a hexanoyl group (—CO—$CH_2CH_2CH_2CH_2CH_3$), and y may be 10 to 10,000, 10 to 9,500, 10 to 9,000, 10 to 8,500, 10 to 8,000, 10 to 7,500, 10 to 7,000, 10 to 6,500, 10 to 6,000, 10 to 5,500, 10 to 5,000, 10 to 4,500, 10 to 4,000, 10 to 3,500, 10 to 3,000, 10 to 2,500, 10 to 2,000, 10 to 1,500, 10 to 1,000, 10 to 900, 10 to 800, 10 to 700, 10 to 600, or 10 to 500.

According to one embodiment, the drug for treating inner ear disease may be a corticosteroid-based drug.

The preparation may be an injectable formulation.

Other contents regarding the formulation can be understood by referring to the contents regarding the pharmaceutical composition.

Advantageous Effects

A pharmaceutical composition for treating inner ear diseases according to one embodiment, when administered intratympanically, can effectively deliver the drug to the inner ear without side effects.

The controlled drug release formulation according to one embodiment, when administered intratympanically, can deliver the drug in a sustained or immediate release manner without side effects.

BRIEF DESCRIPTION OF DRAWINGS

FIG. 1 is a schematic diagram showing a method for synthesis of HGC thermogel, the principal of thermogelation of HGC, and intratympanic administration of a mixture of HGC and dexamethasone for delivery of dexamethasone to the inner ear.

FIG. 2 shows the $^1$H-NMR (2*a*) and ATR-FTIR spectra (2*b*) of GC and HGC, and the solubility of dexamethasone depending on HGC concentration (2*c*).

FIG. 3 shows the results of examining the sol-gel transition of GC, HGC, HGC-DSP, and HGC-DEX at 20 °C and 37 °C. (3*a*), and FE-SEM images of lyophilized HGC, HGC-DSP, and HGC-DEX samples (3*b*).

FIG. 4 shows the temperature-dependent rheological behaviors of GC (4*a*), HGC (4*b*), HGC-DSP0.5 (4*c*), HGC-DEX0.5 (4*d*), HGC-DSP1 (4*e*), and HGC-DEX1 (4*f*).

FIG. 5 shows the in vitro drug release profiles of DSP and HGC-DSP with increasing DSP concentration (5*a*), and the in vitro drug release profiles of DEX and HGC-DEX with increasing DEX concentration (5*b*).

FIG. 6 shows the results of analyzing the intratympanic residual stability of HGC using CT and T2-weighted MRI.

FIG. 7 shows the results of examining the adverse effects of intratympanic administration of HGC through histopathological analysis by H&E staining (7*a*) and whole-mount staining (7*b*). FIG. 7*a* shows histopathologic findings of sections of normal middle ear mucosa (left), middle ear mucosa 21 days after saline injection (middle), and middle ear mucosa 21 days after HGC injection (right). The upper scale bar is 1,000 μm, and the lower scale bar is 50 μm. FIG. 7*b* shows the results of whole-mount staining of auditory epithelium 21 days after HGC injection. Tissues were stained for myosin-VIIa (red), rhodamine phalloidin (green) to visualize auditory hair cells, and actin, and then merged. OHC denotes outer hair cells, IHC denotes inner hair cells, and the scale bar is 50 μm.

FIG. 8*a* shows the results of measuring the concentration of DEX (DSP) in the perilymph fluids of the groups injected intratympanically with DSP, HGC-DSP, and HGC-DEX, and FIG. 8*b* shows the results of quantitatively analyzing DEX (DSP) uptake in cochlear tissue 30 and 90 minutes after intratympanic injection of DSP, HGC-DSP, and HGC-DEX.

FIG. 9 shows SEM images (9*a*) and optical microscope images (9*b*) of dexamethasone-loaded microspheres.

FIG. 10 shows the results of in vitro drug release experiments on HGC in which dexamethasone-loaded microspheres were dispersed. FIG. 10*a* shows the results of an experiment using 023 microspheres, and FIG. 10*b* shows the results of an experiment using 061 and 062 microspheres.

FIG. 11 shows the results of a hydrolysis experiment on drug-loaded microspheres (M-DEX). FIG. 11 shows SEM images of M-DEX over time (after 0, 7, 14, 21, and 28 days).

FIG. 12 shows SEM images of the surfaces and cross-sections of HGC, HGC/DEX, HGC/M-DEX, and HGC/DEX/M-DEX.

FIG. 13 is a graph showing the time-dependent storage stability of HGC as residual weight. FIG. 13 is a graph comparing between the case where HGC was stored in PBS and the case where lysozyme was used as a degradation enzyme.

MODE FOR INVENTION

Hereinafter, one or more embodiments will be described in more detail by way of examples. However, these examples are intended to illustrate one or more embodiments and the scope of the present invention is not limited to these examples.

Experimental Methods

1. Material Preparation

Glycol chitosan (GC, degree of polymerization (DP) ≥200, degree of acetylation=9.34±2.5%, as measured by $^1$H-NMR) was purchased from Wako (Japan). Hexanoic acid anhydride (97%) was purchased from Sigma-Aldrich (USA). Acetone and methanol were supplied by Samchun Chemical (Korea). Dialysis membranes (MWCO=12 to 14 kDa) were purchased from Spectrum Laboratories (USA). Deuterium oxide ($D_2O$) and Dulbecco's phosphate buffered saline (PBS) were purchased from Sigma-Aldrich (USA). Dexamethasone (DEX, micronized) and DEX phosphate disodium salt (DSP) were purchased from Farmabios (Italy) and Steraloids (USA), respectively.

2. Synthesis and Characterization of N-Hexanoyl Glycol Chitosan (HGC)

HGC was synthesized via the N-hexanoylation reaction of glycol chitosan (GC). GC (3 g) and hexanoic acid anhydride (1.106 mL) were dissolved in 700 mL of a mixed solvent of water and methanol (50:50) and magnetically stirred at room temperature for 24 hours. The reaction solution was poured into an excess amount of cold acetone, and the polymerized product, HGC, was precipitated. The product was dialyzed against distilled water using a dialysis membrane (molecular weight cut-off: 12-14 kDa) for 2 days to purify HGC, followed by lyophilization.

The chemical composition of HGC was analyzed by $^1$H-NMR spectroscopy at 600 MHz using an AVANCE III 600 spectrometer (Bruker, Germany). The HGC polymer sample was dissolved in $D_2O$ at 0.5 wt %. The $D_2O$ peak at 4.85 ppm was set as the reference peak. The chemical composition of HGC was characterized by ATR-FTIR using Nicolet iS 5 (Thermo Scientific, USA). The ATR-FTIR spectra of GC and HGC were recorded in a circumstance with 32 scans at a resolution of 4 cm-1 in the frequency range of 4,000 to 750 $cm^{-1}$.

3. Solubility Test

Changes in water solubility of dexamethasone (DEX) with changes in HGC concentration were analyzed. An excessive amount of DEX was added to 3 mL of an aqueous solution of HGC (PBS, HGC concentration=0 to 4%, w/v). The samples were then stirred for 30 minutes and incubated in a shaking water bath (100 rpm, 37 °C) for 24 hours. All the samples were filtered through a syringe filter (0.8 μm) to remove precipitates and then analyzed using a UV-visible spectrophotometer (V-730, JASCO, Korea). The solubility value of DEX was determined using a standard curve of various DEX concentrations obtained at 242 nm. The test was repeated three times.

4. Preparation of Drug-Loaded HGC Thermogels

Drug-loaded HGC thermogels were prepared by simply physically mixing an aqueous solution of HGC (PBS, 4 wt %) with DSP (hydrophilic DEX) or DEX (hydrophobic DEX). First, 40 mg of HGC was dissolved in 1 mL of PBS (pH 7.4) and stored in a refrigerator at 4 °C. DSP or DEX (5 or 10 mg) was added to the HGC solution and mixed by vortexing to obtain DSP-loaded HGC (HGC-DSP) and DEX-loaded HGC (HGC-DEX) samples having a drug concentration of 0.5 or 1.0 wt %.

5. Thermo-Sensitive Sol-Gel Transition

The sol-gel transition behaviors of the HGC thermogel formulations were observed using the tilting tube method at a heating rate of 1 °C/min. The sol-gel transition temperature was determined as the temperature at which the formulation exhibited a non-flowing gel state within 1 minute after tilting the vial. The experiment was performed in triplicate.

6. Rheological Analysis

Rheological analysis of the HGC solution and the drug-loaded HGC solution was performed using a MARS-40 rheometer (Thermo Scientific, Germany). Aqueous solutions of GC, HGC, HGC-DSP and HGC-DEX samples were placed between parallel plates (60 mm diameter and 1 mm gap). Measurements were performed at a frequency of 1 Hz and a constant stress of 10 Pa. The temperature was increased from 10 °C to 45 °C at a heating rate of 0.05 °C/s.

7. In Vitro Drug Release

The in vitro drug release profiles of the thermogel formulations were examined in PBS (pH 7.4) using a dialysis membrane. The prepared thermogel formulations (HGC-DSP and HGC-DEX) having a drug concentration of 0.5 or 1 wt % were placed in dialysis membrane bags (MWCO=12 to 14 kDa, width: 10 mm). Then, the dialysis bags were immersed in 50 mL of PBS and incubated in a shaking water bath (SI-600R, Jeio Tech, Seoul, Korea) at 37 °C and 100 rpm or less.

After incubation, 10 ml of the release medium was taken out and the same amount of fresh medium was added again. The collected samples were analyzed by UV-Vis measurement. The DEX release profile was determined by measuring the UV absorbance of DEX at 242 nm. The experiment was performed in triplicate and data are expressed as mean±SD.

8. Experimental Animals

All animal experiments were approved by the Chungnam National University Committee of Animal Experiments (202006A-CNU-085). Ninety eight male albino guinea pigs, each weighing 200 to 250 g, were used in this study. To analyze the residual stability of the HGC thermogel after injection into the middle ear, twenty animals were used to perform micro-computed tomography (CT) and magnetic resonance imaging (MRI) at various injection time points (1, 3, 7, 14, and 21 days) and to perform histopathological analysis. Seventy two animals were used for perilymph sampling at various time points (30 minutes, 90 minutes, 3 hours, 1 day, 3 days, and 7 days) after middle ear injection of the HGC thermogel. Other six animals were used as normal controls for CT and T2-weighed MRI (N=4) and used for histopathological studies after intratympanic injection of saline on day 21 (N=2).

9. Intratympanic Injection

Before surgery, animals were anesthetized by intramuscular injection of alfaxan (15 mg/mL, Careside) and Rumpun (23 mg/mL, Careside). In addition, 0.5 ml of 1% lidocaine was injected subcutaneously into the postauricular area for local anesthesia. The anesthetized animals were placed in a prone position on a thermoregulated heated pad. After incising the retro auricular, the temporal bone was exposed and the round window membrane was visualized with a surgical microscope (Carl Zeiss OPMI f 170 Surgical Tilting Head connected to a Hitachi KP-D50 color digital microscope camera). Each of the HGC-DSP and HGC-DEX thermogel formulations (sample volume=100 μL, drug concentration=5 mg/mL (corresponding to 0.5 wt %)) was administered to the tympanic membrane using a 26 gauge needle. After injection, the needle was carefully removed, dental cement (Durelon™ Carboxylate Luting Cement, 3M) was applied to the area, and the skin incision was sutured. No animals were sacrificed in this series of experiments.

10. Micro-Computed Tomography: CT and T2-Weighted MRI Imaging

Image analysis was performed at various time points after injection (days 1, 3, 7, 14, and 21) using computed tomography (CT) and T2-weighted magnetic resonance imaging (MRI). CT images were acquired on a Quantum GX2 micro-CT Imaging System (PerkinElmer, Waltham, MA, US). MR images were obtained using 4.7 T BioSpec, 47/40 USR (Bruker Biospin, Germany).

11. Histopathologic Analysis after Intratympanic Injection of HGC Thermogel

To investigate whether the HGC thermogel administered intratympanically has a negative effect on the middle ear, cochlea was obtained from the animals 21 days after intratympanic injection of saline or the HGC thermogel, and inflammation of the middle ear mucosa tissue was assessed. Cochlear samples were placed in 4% paraformaldehyde in PBS for 2 hours, decalcified in EDTA for 3 weeks, embedded in paraffin, serially sectioned at 4 μm thickness, and stained with hemotoxylin and eosin. The stained tissue sections were examined and representative fields were photographed using an optical microscope (Olympus BX51).

To assess the uptake of DEX in the cochlear tissue, animals were sacrificed 30 or 90 minutes after surgery. The tissues were rinsed in PBS for 30 min and incubated for 1 hour in a solution containing 10% normal goat serum (Vector Laboratories, Inc.) and 0.3% Triton X-100 (Sigma-Aldrich Co.) to block nonspecific antibody binding.

The tissues were then stained with rabbit anti-DEX primary antibody (Abcam, Cambridge, MA) at a concentration of 1:200 in blocking solution overnight at 4 °C. After rinsing in PBS for 1 hour, the tissues were incubated with the corresponding Alexa Fluor 594 goat anti-rabbit secondary antibody (Molecular Probes, Eugene, OR) at a 1:200 dilution. After incubation at room temperature for 2 hours, the tissues were rinsed in PBS for 30 minutes and stained with 1:200 diluted Hoestch 33342 (Invitrogen) for 5 minutes. After incubation at room temperature, the tissues were rinsed in PBS for 30 minutes and mounted on glass slides using Crystal Mount (Biomeda). The uptake of the drug in the cochlear tissue was observed using a fluorescence microscope (BX53F2, Olympus, Tokyo, Japan).

To evaluate the survival of cochlear hair cells, the animals were sacrificed 21 days after intratympanic injection of the HGC thermogels. Tissues were fixed in 4% paraformaldehyde in PBS for 30 min at 4 °C. The cochlear bony walls and lateral wall tissues were first removed and the remaining cochlear tissues were prepared for immunostaining. The tissues were rinsed in PBS for 30 minutes and incubated for 1 hour in a PBS solution containing 10% normal goat serum and 0.3% Triton X-100 to block nonspecific antibody binding. After blocking, the tissues were stained with 1:200 diluted monoclonal anti-myosin VIIa primary antibody (Proteus BioSciences, Inc.) overnight at 4 °C. The tissues were rinsed in PBS for 60 minutes. After rinsing, the tissues were stained by incubation with 1:200 diluted Alexa Fluor 594 goat anti-mouse secondary antibody and Alexa Fluor 488 Phalloidin antibody for 2 hours at room temperature. The tissues were rinsed in PBS for 15 minutes. After rinsing, the tissues were mounted on glass slides using Crystal Mount. The tissues were observed using a fluorescence microscope (BX53F2, Olympus, Tokyo, Japan).

12. Measurement of Drug Concentration in Cochlear Perilymph

To assess the concentration of DEX in cochlear perilymph, perilymph sampling was performed at various time points (30 minutes, 90 minutes, 3 hours, 1 day, 3 days, and 7 days) after intratympanic injection of the DEX-loaded HGC thermogel. Under anesthesia, the temporal bone was removed, and the tympanic bulla was washed with 10 mL of saline. Small apical cochleostomy was performed using a sharp pick, and perilymph was collected in hand-held graduated glass capillary tubes (IntraMAPK micropipettes) marked at every 4 μl volume. Cochlear fluid and DEX standard samples were diluted 1:11 with artificial perilymph, and each mixture was diluted again 1:3 with 50% MeOH. All samples were analyzed using an operator system (QTRAP 6500) with a UHPLC/Tandem mass spectrometer (QTRAP 6500 Low Mass BL210251506) to measure the DEX concentration in the perilymph by LC-MS/MS. Each sample was injected onto a C18 column (Atlantis dC18 column) with solvent A, 0.1% formic acid/DW, and solvent B, MeOH. The flow rate was 0.3 ml/min. Data scans were performed with multiple reaction monitoring (MRM).

13. Statistical Analysis

Adjustment of image contrast, superimposition of images, and colorization of monochrome fluorescence images were performed using Adobe Photoshop (version 7.0). Data graphing and all statistical analyses were performed using GraphPad Prism 6 (GraphPad Software, San Diego, CA, USA). Two-way ANOVA was used to measure the DEX concentration. All experiments were repeated multiple times. The differences between groups were considered significant at $p<0.05$ in each case.

According to the Examples below, it has been proven that N-acyl glycol chitosan-based thermogels have better properties for injection into the inner ear than block copolymer-based thermogels such as PEG-PPG and PEG-PLGA in terms of physical stability, biocompatibility, biodegradability, thermogelation, and other biofunctions.

Example 1: Synthesis and Characterization of HGC

Among N-acyl glycol chitosans, N-hexanoyl glycol chitosan (HGC) exhibits sol-gel transition in response to body temperature, and the physicochemical properties and thermogelation properties thereof can be modified by changing the degree of N-hexanoylation (DH). Thus, N-hexanoyl glycol chitosan (HGC) may be considered as a suitable drug delivery platform for intratympanic administration by injection.

N-hexanoyl glycol chitosan (HGC) was synthesized by N-hexanoylation of glycol chitosan (GC) and evaluated as an injectable formulation for inner ear delivery (see FIG. 1)

The results of synthesis of HGC were characterized by H-NMR and ATR-FTIR measurements.

FIG. 2*a* shows $^1$H-NMR results for HGC and GC. The $D_2O$ peak at 4.85 ppm was set as a reference peak for analysis. The peak appearing at 3.3 to 4.0 ppm corresponds to the protons (H-2 to H-8) of the glucopyranosyl ring, and the peak appearing at 2.7 ppm is due to the proton of the primary amine residue. These are common peaks for GC and HGC. Among the characteristic H peaks of HGC, 0.8 ppm ($—CH_3$) corresponds to a methyl proton, and the peaks at 1.3 ppm ($—CH_2—CH_2—CH_3$), 1.6 ppm ($—CO—CH_2—CH_2—$), and 2.3 ppm ($—CO—CH_2—$) correspond to the methylene proton of the hexanoyl group. The degree of hexanoylation was calculated to be about 36% of the integrated value of the proton peaks of the glucopyranosyl ring and the hexanoyl group.

FIG. 2*b* shows the results of analyzing the chemical structure of HGC by ATF-FTIR analysis. A broad peak corresponding to the stretching vibration of the hydroxy group appeared at 3,400 $cm^{-1}$, which overlapped with the N—H stretching vibration in the same region. The characteristic peak of HGC appeared at 2,890 $cm^{-1}$, which is attributed to the CH stretching vibration of the methyl and methylene groups of the hexanoyl group. The absorption peak due to the amino bending vibration of GC was observed at 1596 $cm^{-1}$, while the absorption peaks of HGC was observed at 1,655 $cm^{-1}$ and 1,555 $cm^{-1}$, which correspond to the carbonyl stretching vibration and amide II bending vibration, respectively, indicating that the N-hexanoylation reaction of GC was successfully performed.

The HGC polymer is composed of a hydrophilic GC backbone and a hydrophobic hexanoyl group and is amphiphilic in nature, and thus it is expected that the HGC polymer can be loaded with both hydrophilic and hydrophobic drugs.

The solubilization effect of HGC on hydrophobic dexamethasone (DEX) was evaluated below.

FIG. 2*c* shows the solubility of dexamethasone in PBS as a function of the concentration of HGC (0 to 4 wt %). When the concentration of HGC was 0 wt %, the water solubility of dexamethasone was 64 μg/ml. As the concentration of HGC increased, the solubility of dexamethasone increased, and when the concentration of HGC was 4 wt %, the solubility of dexamethasone increased to 221 μg/ml (about 4 times). This indicates that the HGC thermogel improves the water solubility of dexamethasone (DEX).

Example 2: Preparation of Drug-Loaded Thermogels

Table 1 below shows the chemical compositions of drug-loaded thermogels.

TABLE 1

| Thermogel samples | Polymer conc. (wt %) | Drug conc. (wt %) | Sol-gel transition (° C.) $T_{gel}$[a] | $T_{gel}$[b] |
|---|---|---|---|---|
| HGC | 4.0 | — | 32 | 30.7 |
| HGC-DSP 0.5 | | 0.5 | 30 | 27.3 |
| HGC-DSP 1.0 | | 1.0 | 25 | 22.0 |
| HGC-DEX 0.5 | | 0.5 | 30 | 29.7 |
| HGC-DEX 1.0 | | 1.0 | 27 | 25.6 |

[a]The sol-gel transition temperature determined by tube tilting method
[b]The sol-gel transition temperature determined by rheological measurement As listed in Table 1 above, drug-loaded thermogels were prepared by simply mixing an aqueous solution of HGC (4 wt %) and DSP or DEX (0.5 wt % and 1.0 wt %).

DSP is a hydrophilic form of DEX and has high solubility in aqueous solvents. DSP was well mixed with HGC, thus preparing transparent HGC-DSP mixtures (see FIG. 3*a*).

On the other hand, because DEX has low solubility, the HGC-DEX mixtures were not transparent. However, referring to FE-SEM images of the surfaces and cross-sections of lyophilized samples of gelled HGC-DEX, it was observed that micronized DEX particles were uniformly dispersed in the thermogel matrix.

All the HGC-DEX thermogels were shown to stably maintain drug suspensions without aggregation or precipitation. Therefore, HGC has amphiphilic properties and effectively disperses a hydrophobic drug therein, and thus it may be used as an injectable formulation of a hydrophobic drug.

Example 3: Thermo-Sensitive Sol-Gel Transition

The thermo-sensitive sol-gel phase transition behaviors of HGC, HGC-DSP, and HGC-DEX were analyzed by the tube tilting method and rheological analysis.

FIG. 3*a* shows images of aqueous solutions of GC, HGC, HGC-DSP, and HGC DEX (4 wt %, PBS) at 20 °C and 37 °C. No phase transition was observed in GC. The HGC solution showed a clear phase transition from a flowable sol state to a non-flowable gel state as the temperature increased to 37 °C. HGC was observed to exhibit thermogelation at about 32 °C.

The sol-gel transition of HGC-DSP and HGC-DEX was observed to determine whether the presence of hydrophilic DSP or hydrophobic DEX could affect the thermogelation behavior of HGC. Both HGC-DSP and HGC-DEX showed a slightly lower gelation temperature than HGC, and the gelation temperature decreased as the concentration of the drug increased. This may be because the mixing of DSP (sodium phosphate salt form of DEX) or hydrophobic DEX promoted hydrophobic interactions between hexanoyl groups.

The viscoelastic properties, elastic modulus (G') and loss modulus (G") of GC, HGC, HGC-DSP and HGC-DEX were observed through rheological experiments in the temperature range of 10 to 45 °C. The crossover temperature between G' and G" was defined as the gelation point to determine the sol-gel phase transition.

Referring to FIG. 4, the G' value of the GC solution was consistently lower than the G" value without a crossover point over the entire temperature range, indicating that no heat-sensitive sol-gel transition occurred in the GC solution. However, the G' values of HGC, HGC-DSP, and HGC-DEX were lower than the G" values at the initial temperature, but increased rapidly as the temperature increased, so that the G' values became higher than the G" values. For HGC-DSP and HGC-DEX, the G' and G" values cross at lower temperatures than HGC, and these results are consistent with the results from the previous tube tilting method.

Example 4: In Vitro Release Kinetics

In vitro drug release tests were performed on hydrophilic DSP, hydrophobic DEX, DSP-loaded HGC (HGC-DSP), and DEX-loaded HGC (HGC-DEX) in PBS at 37 °C.

Referring to FIG. 5*a*, the DSP and HGC-DSP formulations completely released the drug within 10 hours regardless of the drug concentration (0.5 or 1.0 wt %). The HGC-DSP thermogel showed slightly delayed release compared to DSP, but was not effective in delaying the release rate because DSP is a small molecule drug having high water solubility.

Meanwhile, the HGC-DEX formulation showed various drug release profiles in the range of 4 to 14 days depending on the drug concentration (0.5, 1.0, 2.0, and 4.0 wt %). The release rates of HGC-DEX 0.5 and HGC-DEX 1.0 were faster than that of the free DEX form under the same concentration conditions due to the solubilization effect of the HGC thermogel, which can accelerate the release behavior. HGC-DEX 2 and HGC-DEX 4, which have higher drug concentrations, showed slower release behavior than HGC-DEX 0.5 and HGC-DEX 1.0 having lower drug concentrations, and this may be because when the drug is loaded at a high concentration, more time is needed for the drug to be solubilized and released. Referring to the above results, the HGC thermogel formulation can be optimized to release the hydrophobic drug at an appropriate rate and dose as needed.

Example 5: Evaluation of Intratympanic Residual Stability

The HGC thermogel can improve drug uptake in the inner ear by improving the residual stability of DEX in the middle ear cavity. This is because thermogelation can prevent early leakage of the drug through the Eustachian tube and prolong the residence time of the drug.

In an in vivo experiment, the residual stability of the HGC thermogel in the middle ear cavity was first evaluated by CT and T2-weighted MRI Referring to FIG. 6, the HGC thermogel injected intratympanically remained in the middle ear cavity of the guinea pig for more than 21 days (3 weeks). Referring to the experimental results, it can be seen that the HGC-based thermogel has the advantage of a long in vivo residence time, and has an advantage in that the contact time between the drug loaded therein and the round window membrane increases so that the drug can be continuously delivered to the inner ear.

Example 6: Evaluation of Safety of HGC

Whether intratympanic administration of HGC had an adverse effect was examined by histopathological analysis and observation of the survival of auditory hair cells.

Histological evaluation of the middle ear and inner ear was performed 21 days after intratympanic administration of HGC. Inflammation of the mucosa in the middle ear was detected using hematoxylin and eosin (H&E) staining. Referring to the H&E staining results in FIG. 7*a*, in the group 21 days after intratympanic injection of the HGC thermogel, no evidence of mucosal inflammatory responses, including middle ear edema and fibrosis, was observed.

Referring to FIG. 7*b*, whole-mount staining of inner hair cells (IHC) and outer hair cells (OHC) showed no cell loss or death in all turns of the cochlea.

The above data suggest that the HGC thermogel has no adverse effects on the middle or inner ear. In fact, no inflammatory response in the middle ear mucosa of the guinea pig and no loss of auditory hair cells in the inner ear of the guinea pig were observed. The day after intratympanic injection of the HGC thermogel, all the guinea pigs did not exhibit pathological vestibular behavior such as rolling and moved normally. Therefore, the HGC thermogel is expected to have no side effects such as acute inflammation, progression of middle ear fibrosis, or hearing changes even when injected intratympanically, and may be a safe means for local drug delivery to the inner ear.

Example 7: Evaluation of Inner Ear Drug Delivery Effect of HGC Thermogel

The effect of the HGC thermogel formulation was evaluated by administering HGC-DEX intratympanically and observing changes in the DEX concentration in intracochlear perilymph and DEX distribution in cochlear tissue. Dexamethasone was chosen as a model drug because it has anti-inflammatory and hair cell protective effects and is one of the most commonly used drugs for treating inner ear diseases.

30 minutes, 90 minutes, 3 hours, 1 day, 3 days, or 7 days after intratympanic injection of DSP alone, HGC-DSP (0.5 wt % of DSP), or HGC-DEX (0.5 wt % of DEX), perilymph was collected from the cochlea and the DEX concentration was measured using liquid chromatography/tandem mass spectrometry (LC-MS/MS).

Referring to FIG. 8*a*, in the groups that received intratympanic injections of DSP, HGC-DSP, and HGC-DEX, respectively, significant DEX concentrations were detected in the perilymph fluid starting 30 minutes after injection. The aqueous formulation containing DSP alone showed the highest initial concentration 30 minutes after administration, but the concentration decreased after 90 minutes, and DSP was not detected after 3 hours. On the other hand, the thermogel formulations HGC-DSP and HGC-DEX were both able to maintain high drug concentrations for a longer period of time. In particular, the DEX concentration in the HGC-DEX formulation-administered group reached its peak at 90 minutes after administration and was shown to be higher than that in the DSP control group. In addition, in this group, a significant DEX concentration was detected even 1 day after administration.

Referring to the results of analyzing the intensity of immunohistochemical staining as shown in FIG. 8*b*, drug uptake in cochlear tissue significantly increased in the HGC-DEX-administered group compared to the DSP alone-administered group and the HGC-DSP-administered group. These results indicate that the HGC thermogel formulation loaded with the hydrophobic drug can significantly improve drug uptake in cochlear tissue. The formulation of DSP alone may have high initial uptake, but the duration thereof is very short because it is quickly discharged through the Eustachian tube. In contrast, the thermogel formulations can remain in a gel state in the inner ear cavity for a longer time and have a longer contact time with the round window membrane (RWM), which can increase the efficiency of drug delivery to the inner ear. However, the above animal experiment results are the results of measuring the drug uptake amount, and the uptake amount varies depending on the characteristics and uptake time of the released drug, so the drug release rate and uptake amount do not necessarily match with each other. That is, the uptake amount suggests possible sustained release of the drug in the tympanic cavity, but does not directly indicate the rate of sustained release.

Referring to the above in vitro drug release test, the drug release rate of the HGC-DEX thermogel was dependent on the drug concentration, and the higher the concentration of the loaded drug, the slower the release rate was. Therefore, if an HGC thermogel formulation having a higher drug concentration is used, the effective drug concentration will be maintained for a longer period of time. Thus, the HGC thermogel formulation can be considered an effective and useful means for local drug delivery to the inner ear.

Referring to the above experimental results, the HGC-based thermogel was found to be an intratympanically injectable drug delivery platform that can be loaded with both a hydrophobic drug (e.g., dexamethasone) and a hydrophilic drug (e.g., dexamethasone phosphate disodium salt (DSP)). The HGC-based thermogel could be loaded with the drug by a simple method of physically mixing the thermogel in a sol state with the drug, and in particular, the hydrophobic drug (DEX) was effectively dispersed and solubilized therein. Referring to the animal experiment results, it was confirmed that the HGC thermogel remained in the middle ear and inner ear cavity for up to 21 days without significant cytotoxicity or inflammation, suggesting that it has excellent residual safety and is suitable for maintaining the drug concentration in the inner ear at a high level for a long time. In addition, the HGC thermogel formulation exhibited diverse release kinetics depending on the drug type and concentration. Referring to the in vitro drug release test, HGC thermogel could release the drug in an immediate release manner when loaded with 0.5 wt % or 1.0 wt % of the drug, and could release the drug continuously for 2 weeks when loaded with 2 wt % or 4 wt % of the drug. In addition, the HGC thermogel loaded with 0.5 wt % of the drug released the drug for 1 day as a result of the intratympanic administration test.

Since it was confirmed in the in vitro drug release test that the HGC thermogel released the drug in an immediate or sustained release manner depending on the concentration of the drug, it is expected that the HGC thermogel can release the drug sustainedly in the tympanic cavity depending on the concentration of the drug. Therefore, the HGC thermogel was found to have great potential as an effective and safe platform for drug delivery to the inner ear.

Example 8-1: HGC Thermogel Containing Drug-Loaded Microspheres

Drug-loaded microspheres made of a polymer having excellent biocompatibility and biodegradability can be used for sustained release of drugs. However, the microspheres have a disadvantage in that, since they can easily move to other areas even when injected intratympanically, it is difficult for the microspheres to deliver the drug continuously while remaining in the tympanic cavity.

To overcome this disadvantage, HGC thermogels containing dexamethasone-loaded microspheres dispersed therein were fabricated and their in vitro drug release rates were measured.

Four types of microspheres (GB-5313-023, GB-5313-061, GB-5313-062, and GB-5313-075) with differences in terms of formulation method, drug content, and particle size were prepared (hereinafter referred to as 023, 061, 062, and 075). Their compositions are shown in Tables 2 and 3 below.

TABLE 2

| | GB-5313-023/061/075 | GB-5313-062 |
|---|---|---|
| Polymer | RESOMER RGS02H | RESOMER RG503H |
| Composition (LA:GA) | 50:50 | 50:50 |
| Molecular weight (g/mol) | 13,000~15,000 | 24,000-38,000 |

TABLE 3

| Lot No. | Formulation method | Polymer | Drug content (wt %) | Particle size (D50, μm) |
|---|---|---|---|---|
| GB-5313-023 | O/W | 502H | 14.8 | 27.04 |
| GB-5313-061 | S/O/W | 502H | 24.4 | 31.78 |
| GB-5313-062 | S/O/W | 503H | 12.5 | 33.28 |
| GB-5313-075 | O/W | 502H | 16.4 | 21.88 |

Here, the particle size ($D_{50}$) means the average diameter of 50% of the particles.

The S/O/W denotes Solid-in-Oil-in-Water Emulsion, and each S/O/W was prepared by adding the solid drug(S) encapsulated with 061 or 062 to the polymer/oil phase (O) and adding water thereto to form an emulsion. The O/W was prepared by adding the non-encapsulated solid drug to the polymer/oil phase (O) and adding water thereto to form an emulsion.

The 061 is a formulation that is expected to release the drug faster due to its higher drug content than the 023. The 062 is a formulation that is expected to release the drug more slowly because it contains the 503H polymer having a higher molecular weight than the 023. The 075 is a formulation prepared under the same conditions as the 023, except that the particle size is smaller. The fabricated microspheres are shown in FIG. 9.

An in vitro drug release test was conducted as follows.

023 microspheres loaded with dexamethasone were mixed with 4 wt % of HGC hydrogel. An in vitro drug release test was conducted in a PBS (pH 7.4, 50 ml) environment in the same manner as in Example 4. Sampling was performed at days 0, 0.5, 1, 2, 4, 7, 14, 21, 28, and 30. The dialysis membrane had a thickness of 10 mm and a MWCO of 12 to 14 kDa. The in vitro drug release test conditions for 023 microspheres, etc. are shown in Table 4 below.

TABLE 4

| Sample | HGC (mg) | Drug (mg) | Microspheres (mg) | Total drug (mg) | Sample volume (ml) |
|---|---|---|---|---|---|
| Free DEX | — | 5 | — | 5 | 1 |
| HGC + DEX | 40 | 5 | — | | |
| 023 + HGC | 40 | — | 33.78 (for 5 mg drug) | | |
| 023 + DEX + HGC | 40 | 2.5 | 16.89 (for 2.5 mg drug) | | |
| 023 | — | — | 33.78 (for 5 mg drug) | | |

Dexamethasone-loaded 061 or 062 microspheres were mixed with 4 wt % of HGC hydrogel, and an in vitro drug release test therefor was conducted in the same manner as the test for the 023. The in vitro drug release test conditions for 061 microspheres, etc. are shown in Table 5 below.

TABLE 5

| Sample | HGC (mg) | Drug (mg) | Microspheres (mg) | Total drug (mg) | Sample volume (ml) |
|---|---|---|---|---|---|
| 061 | — | — | 20.5 (5 mg drug) | 5 | 1 |
| 061 + HGC | 40 | — | 20.5 (5 mg drug) | | |
| 061 + DEX + HGC | 40 | 2.5 | 10.25 (2.5 mg drug) | | |
| 062 | — | — | 40 (5 mg drug) | | |
| Free DEX | — | 5 | — | | |

Referring to FIG. 10*a*, 023+HGC (HGC having 023 microspheres (DEX-loaded) dispersed therein) showed delayed release compared to HGC+DEX or 023+HGC+DEX (HGC having DEX-loaded 023 and DEX itself dispersed therein). In the case of 023+HGC+DEX, immediate release occurred for the first 2 days, and then the release rate slowed down starting from day 3 and sustained release occurred for more than 20 days. This is because DEX loaded in HGC was released immediately due to the solubilization effect of HGC, and DEX loaded in the 023 was released in a sustained release manner. These drug release characteristics may be useful for patients in need of a combination of initial immediate release and sustained release.

Referring to FIG. 10*b*, in the case of HGC (061+HGC) having 061 microspheres (DEX-loaded) dispersed therein, sustained release occurred, and in the case of 061+HGC+DEX, immediate release occurred for the first 2 days, and then the release rate slowed down starting from day 3 and sustained release occurred for more than 20 days, which is also as explained above.

Referring to the above experimental results, the release of DEX loaded in HGC can be promoted due to the solubilization effect of HGC, and DEX can be released sustainedly by being loaded in microspheres made of a biocompatible polymer, and when both DEX and DEX-loaded microspheres are mixed with HGC, high release can occur initially and long-term sustained release can also occur. In addition, since HGC, when injected intratympanically, gels in response to body temperature, thereby inhibiting the drug from moving elsewhere, it is possible to achieve desired drug release characteristics by mixing HGC with one appropriately selected from a drug, a drug loaded in microspheres, or a combination thereof.

Example 8-2: Analysis of Physical Properties of HGC Thermogel Containing Drug-Loaded Microspheres The physical properties of drug-loaded microspheres and the HGC thermogel containing the same were analyzed. Dexamethasone was used as the drug, and PLGA was used as the microspheres.

LA (lactide) and GA (glycolide) were dissolved in dichloromethane, and then dexamethasone was suspended in the solution, thus preparing a dispersed phase. The dispersed phase was injected into an aqueous solution of PVA (0.5% w/w) as a continuous phase using a membrane emulsification system (LDC-1, Micropore Technologies), thus preparing an emulsion. The organic solvent was removed from the emulsion to obtain solidified microspheres, which were then washed with distilled water to obtain drug-loaded microspheres (M-DEX).

First, the loading content and encapsulation efficiency of the drug in the microspheres were analyzed. A solution obtained by dissolving 10 mg of dexamethasone in 1 mL of DMSO, followed by dilution with 50% CAN, was used as a standard solution, and a solution obtained by dissolving 10 mg of the microspheres in 1 mL of DMSO, followed by 1,250-fold dilution with 50% CAN, was as a sample solution. Using these solutions, measurements were repeated three times. The content and encapsulation efficiency of dexamethasone were determined by measuring the absorbance of dexamethasone at 254 nm by HPLC (CM5000, Hitachi) using 50% CAN as a mobile phase. The content of the drug was calculated as a percentage of the amount of dexamethasone contained in the microspheres relative to the amount of the microspheres, and the content of the drug was shown to be about 33.3%. The encapsulation efficiency of the drug was calculated as a percentage of the amount of dexamethasone contained in the microspheres relative to the initial amount of dexamethasone, and the encapsulation efficiency was shown to be about 83.3%.

FIG. 11 shows the results of conducting a hydrolysis experiment on the microspheres over time. The morphological characteristics of the drug-loaded microspheres (M-DEX) were investigated through SEM observation. Referring to FIG. 11, it was shown that the microspheres exhibited a uniform and distinct spherical particle shape immediately after preparation (day 0), and the loaded drug particles were also on the surface of the microspheres. It was confirmed that, after 7 days, the exposed drug particles disappeared and wrinkles appeared on the surface of the microspheres, and after 21 to 28 days, the microspheres were biodegraded.

Additionally, according to the same method as the above Example, a HGC thermogel (HGC), a dexamethasone-loaded HGC thermogel (HGC/DEX), a formulation (HGC/M-DEX) comprising the HGC thermogel and dexamethasone-loaded microspheres, and a formulation (HGC/DEX/M-DEX) comprising the dexamethasone-loaded HGC thermogel and dexamethasone-loaded microspheres were prepared as shown in Table 6, and the morphological characteristics and physical properties thereof were investigated.

TABLE 6

| | Polymer concentration (wt %) | Drug concentration (wt %) | Sol-gel transition (° C.) $T_{gel}$* | $T_{gel}$** |
|---|---|---|---|---|
| HGC | 3.0 | — | 28 | 28.1 |
| HGC/DEX | 3.0 | 2.0 | 26 | 26.9 |
| HGC/M-DEX | 3.0 | 2.0 | 24 | 26.0 |
| HGC/DEX/M-DEX | 3.0 | 2.0 | 25 | 26.9 |

In Table 6 above, $T_{gel}$* is the transition temperature determined by the tube tilting method, and $T_{gel}$** is the transition temperature determined by rheological measurement. In the case of HGC without the drug, a sol-gel phase transition was observed at about 28 °C, and in the case of the drug-loaded formulations, a sol-gel phase transition was observed at 24 to 26 °C. This indicates that gelation occurred at a lower temperature because hydrophobic interactions were enhanced due to the introduction of the hydrophobic drug or the microspheres.

FIG. 12 shows SEM images of the surfaces and cross-sections of HGC, HGC/DEX, HGC/M-DEX, and HGC/DEX/M-DEX. Referring to FIG. 12, it was shown that, in HGC, the inherent porous structure of the hydrogel was observed, and in HGC/DEX, drug particles were uniformly dispersed on the surface of the porous structure. In HGC/M-DEX and HGC/DEX/M-DEX, the presence of microspheres trapped in the porous network structure could be seen.

FIG. 13 is a graph showing the storage stability of HGC. As a result of storing HGC in PBS and observing the same over time, the weight of HGC initially increased due to swelling and then gradually decreased, but the residual weight was maintained at about 70% or more even after 15 days. These results are contrary to the fact that conventional thermogels based on synthetic polymers such as poloxamer dissolve within a few hours. In addition, it was shown that HGC was biodegradable within one day when stored in PBS in the presence of lysozyme, a degradation enzyme, indicating that the HGC thermogel is useful as a material having both stability and biodegradability.

An aqueous solution formulation of DSP was used as a water-soluble drug control, and it was shown that the control completely released the drug quickly within a few hours. On the other hand, dexamethasone (DEX) was used as a hydrophobic drug control, and dexamethasone exhibited sustained release compared to DSP, but it was believed to have a solubility limit due to its poor solubility rather than controlled release. HGC/DEX exhibited more effective release behavior than the hydrophobic drug control (DEX) by virtue of the solubilization effect of HGC. The HGC/M-DEX and HGC/DEX/M-DEX formulations exhibited sustained release for about a month at rates similar to that of HGC/DEX. Since the formulation comprising g the microspheres can exhibit stable and controllable release behavior, sustained drug release of this formulation is easier to control than that of the HGC/DEX formulation, which is dependent on the drug concentration.

Referring to the above-described experimental results, the release of DEX loaded in HGC can be promoted due to the solubilization effect of HGC, and the formulation containing the microspheres and the formulation comprising a mixture of the thermogel and the microspheres have high drug encapsulation efficiency due to the introduction of the microspheres, drug release therefrom is easily controlled, and it is possible to control the drug release rate therefrom from several weeks to several months by controlling the biodegradability thereof.

The invention claimed is:

1. A pharmaceutical composition for treating inner ear disease by administration through intratympanic injection, comprising a polymer having a unit represented by Formula 1 below, and a drug for treating inner ear disease,
   wherein the polymer has a degree of polymerization (DP) of 200 to 400,
   wherein the drug for treating inner ear disease is dexamethasone, dexamethasone phosphate, or a pharmaceutically acceptable salt thereof,
   wherein the pharmaceutical composition comprises the polymer in an amount of 0.5 to 4 wt %,
   wherein the pharmaceutical composition comprises the drug for treating inner ear disease in an amount of 0.5 to 4 wt %,
   wherein the polymer undergoes a sol-gel phase transition depending on temperature:

[Formula 1]

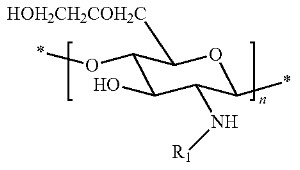

wherein $R_1$ is a hexanoyl group, and n is 10 to 10,000.

2. The pharmaceutical composition according to claim 1, wherein a temperature at which the sol-gel phase transition occurs is 30 to 34 °C.

3. The pharmaceutical composition according to claim 1, wherein the pharmaceutical composition releases a hydrophilic drug in an immediate release manner and releases a hydrophobic drug in a sustained release manner.

4. The pharmaceutical composition according to claim 1, wherein the drug for treating inner ear disease is the drug itself, a form in which the drug is loaded in microspheres, or a combination thereof.

5. The pharmaceutical composition according to claim 4, wherein the microspheres comprise a biodegradable polymer having a molecular weight of 5,000 to 200,000, and have a diameter of 10 to 100 μm.

6. The pharmaceutical composition according to claim 1, wherein the inner ear disease is at least one selected from the group consisting of Meniere's disease, sensorineural hearing loss, ototoxic hearing loss, noise-induced hearing loss, age-related heating loss, tinnitus, vestibular neuritis, auditory nerve tumor, otosclerosis, traumatic hearing loss, and autoimmune inner ear disease.

7. A controlled drug release formulation comprising a polymer having a unit represented by Formula 1 below, and a drug for treating inner ear disease dispersed in the polymer,
   wherein the polymer has a degree of polymerization (DP) of 200 to 400,
   wherein the drug for treating inner ear disease is dexamethasone, dexamethasone phosphate, or a pharmaceutically acceptable salt thereof,
   wherein the pharmaceutical composition comprises the polymer in an amount of 0.5 to 4 wt %,
   wherein the pharmaceutical composition comprises the drug for treating inner ear disease in an amount of 0.5 to 4 wt %,
   wherein the formulation undergoes a sol-gel phase transition after intratympanic injection thereof:

[Formula 1]

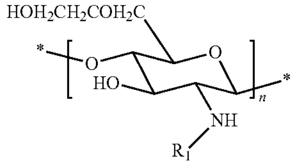

wherein $R_1$ is a hexanoyl group, and n is 10 to 10,000.

* * * * *